US011376005B2

(12) United States Patent
Judy et al.

(10) Patent No.: US 11,376,005 B2
(45) Date of Patent: Jul. 5, 2022

(54) TISSUE-ENGINEERED ELECTRONIC PERIPHERAL NERVE INTERFACE

(71) Applicant: UNIVERSITY OF FLORIDA RESEARCH FOUNDATION, INCORPORATED, Gainesville, FL (US)

(72) Inventors: Jack Judy, Gainesville, FL (US); Christine E. Schmidt, Gainesville, FL (US); Kevin Otto, Gainesville, FL (US); Carlos Rinaldi, Gainesville, FL (US); Cary A. Kuliasha, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 449 days.

(21) Appl. No.: 15/987,388

(22) Filed: May 23, 2018

(65) Prior Publication Data
US 2018/0338765 A1  Nov. 29, 2018

Related U.S. Application Data

(60) Provisional application No. 62/545,019, filed on Aug. 14, 2017, provisional application No. 62/510,467, filed on May 24, 2017.

(51) Int. Cl.
*A61B 17/11* (2006.01)
*A61L 31/04* (2006.01)
(Continued)

(52) U.S. Cl.
CPC ........ *A61B 17/1128* (2013.01); *A61L 31/022* (2013.01); *A61L 31/028* (2013.01);
(Continued)

(58) Field of Classification Search
CPC ................ A61N 1/0551; A61N 1/0556; A61B 17/1128; A61L 2430/32; A61L 2300/412
See application file for complete search history.

(56) References Cited

U.S. PATENT DOCUMENTS 8,668,863 B2  3/2014  Zawko et al.
8,946,194 B2  2/2015  Mayes et al.
(Continued)

FOREIGN PATENT DOCUMENTS

WO   WO 2017011050 A2   1/2017

OTHER PUBLICATIONS

Desai, Vidhi et al. "Chronic Sensory-Motor Activity in Behaving Animals Using Regenerative Multi-Electrode Interfaces," *In 2014 36th Annual International Conference of the IEEE Engineering in Medicine and Biology Society*, pp. 1973-1976, Aug. 2014. IEEE.
(Continued)

*Primary Examiner* — Todd J Scherbel
(74) *Attorney, Agent, or Firm* — Alston & Bird LLP

(57) ABSTRACT

Tissue-engineered electronic peripheral nerve interface (TEENI) devices, methods of using TEENI devices, and systems using TEENI devices are provided. In particular, TEENI devices include a support member having a length,
(Continued)

at least one thread set comprising a plurality thread set arms having a plurality of electronic leads running through the thread set arms and being fully encapsulated within the support member, and a plurality of electrodes fixed to the plurality of thread set arms.

15 Claims, 32 Drawing Sheets

(51) Int. Cl.
  A61L 31/14      (2006.01)
  A61L 31/16      (2006.01)
  A61N 1/05       (2006.01)
  A61L 31/02      (2006.01)
  A61B 17/00      (2006.01)
  A61N 1/36       (2006.01)
(52) U.S. Cl.
  CPC .......... *A61L 31/041* (2013.01); *A61L 31/145* (2013.01); *A61L 31/148* (2013.01); *A61L 31/16* (2013.01); *A61N 1/0551* (2013.01); *A61B 2017/0003* (2013.01); *A61B 2017/00004* (2013.01); *A61B 2017/00017* (2013.01); *A61B 2017/00526* (2013.01); *A61B 2017/00876* (2013.01); *A61B 2017/1132* (2013.01); *A61L 2300/412* (2013.01); *A61N 1/36103* (2013.01)

(56) References Cited

U.S. PATENT DOCUMENTS

| | | |
|---|---|---|
| 9,095,558 B2 | 8/2015 | Mayes et al. |
| 2011/0237921 A1* | 9/2011 | Askin, III .............. A61N 1/375 600/377 |
| 2015/0174396 A1* | 6/2015 | Fisher ................ A61B 5/04001 600/377 |
| 2018/0133372 A1* | 5/2018 | Rinaldi .................. A61L 27/52 |

OTHER PUBLICATIONS

Lago, Natalia et al. "Neurobiological Assessment of Regenerative Electrodes for Bidirectional Interfacing Injured Peripheral Nerves," *IEEE Transactions on Biomedical Engineering*, vol. 54, No. 6, Pt 1, pp. 1129-1137, Jun. 2007. DOI:10.1109/TBME.2007.891168.
Ordonez, Juan S. et al. "Improved Polyimide Thin-Film Electrodes for Neural Implants," *2012 Annual International Conference of the IEEE Engineering in Medicine and Biology Society*, vol. 2012, pp. 5134-5137, Aug. 28-Sep. 1, 2012, San Diego, California.
Raspopovic, Stanisa et al. "Restoring Natural Sensory Feedback in Real-Time Bidirectional Hand Prostheses," *Science Translation Medicine*, vol. 6, No. 222:222ra19, Feb. 5, 2014, (11 pages). DOI: 10.1126/scitranslmed.3006820.

* cited by examiner

MULTI-CHANNEL ZERO INSERTION FORCE (ZIF) CONNECTOR

MICROFABRICATED THREAD-SET ASSEMBLED WITH CUSTOM-MADE PCB

ASSEMBLE TEEM WITH PCB
TOP JIG TO LOAD TEEM
BASE JIG TO HOLD PCB

TEEM
THREAD-SET

US 11,376,005 B2

TISSUE-ENGINEERED ELECTRONIC PERIPHERAL NERVE INTERFACE

CROSS-REFERENCE TO RELATED APPLICATION

This application claims the benefit of priority to U.S. Application No. 62/510,467 filed on May 24, 2017, and U.S. Application No. 62/545,019 filed on Aug. 14, 2017, the content of which is incorporated herein by reference in its entirety for all purposes.

STATEMENT REGARDING FEDERALLY SPONSORED RESEARCH OR DEVELOPMENT

This invention was made with government support under HR0011-15-2-0030 awarded by Department of Defense/Defense Advanced Research Projects Agency. The government has certain rights in the invention.

TECHNICAL FIELD

The presently-disclosed invention relates generally to nerve-scaffold technology and methods and systems using the same, and more particularly to tissue-engineered electronic peripheral nerve interface technology and methods and systems using the same.

BACKGROUND

Nerve-scaffold technology has advanced to the point where patients with severe nerve damage, who might otherwise suffer from chronic, stabbing, radiating, and debilitation pain, numbness, loss of sensation, and partial or full loss of limb movement, are now able to recover function. However, such nerve-scaffold technology has not yet been used to serve patients for which limb amputation is unavoidable.

Accordingly, there still exists a need for nerve-scaffold technology to be used in patients with limb amputation.

BRIEF SUMMARY OF THE INVENTION

One or more embodiments of the invention may address one or more of the aforementioned problems. Certain embodiments provide devices, systems, and methods for regenerating a transected nerve to form a regenerated nerve, detecting and recording neural activity in the regenerated nerve, and stimulating the regenerated nerve. In one aspect, a tissue-engineered electronic peripheral nerve interface (TEENI) device is provided. The TEENI device may include a support member having a length, at least one thread set comprising a plurality of thread set arms having a plurality of electronic leads running through the thread set arms, the thread set arms being fully encapsulated within the support member, and a plurality of electrodes fixed to the thread set arms.

In another aspect, a system for supporting a transected nerve is provided. The system may include a TEENI device, a control element, a connecting element comprising a plurality of electronic leads connected to the TEENI device and extending to the control element, and a downstream element configured to communicate with the transected nerve via the control element. The TEENI device may include a support member, a thread set comprising a plurality of thread set arms having a plurality of electronic leads running through the thread set arms, the thread set arms being fully encapsulated within the support member, and a plurality of fixed electrodes to the plurality of thread set arms.

In yet another aspect, a method for supporting a transected nerve is provided. The method may include providing a TEENI device, suturing the TEENI device to the transected nerve, and regenerating the transected nerve to form a regenerated nerve. The TEENI device may include a support member, a thread set comprising a plurality of thread set arms having a plurality of electronic leads running through the thread set arms, the thread set arms being fully encapsulated within the support member, and a plurality of electrodes fixed to the plurality of thread set arms.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 17A:
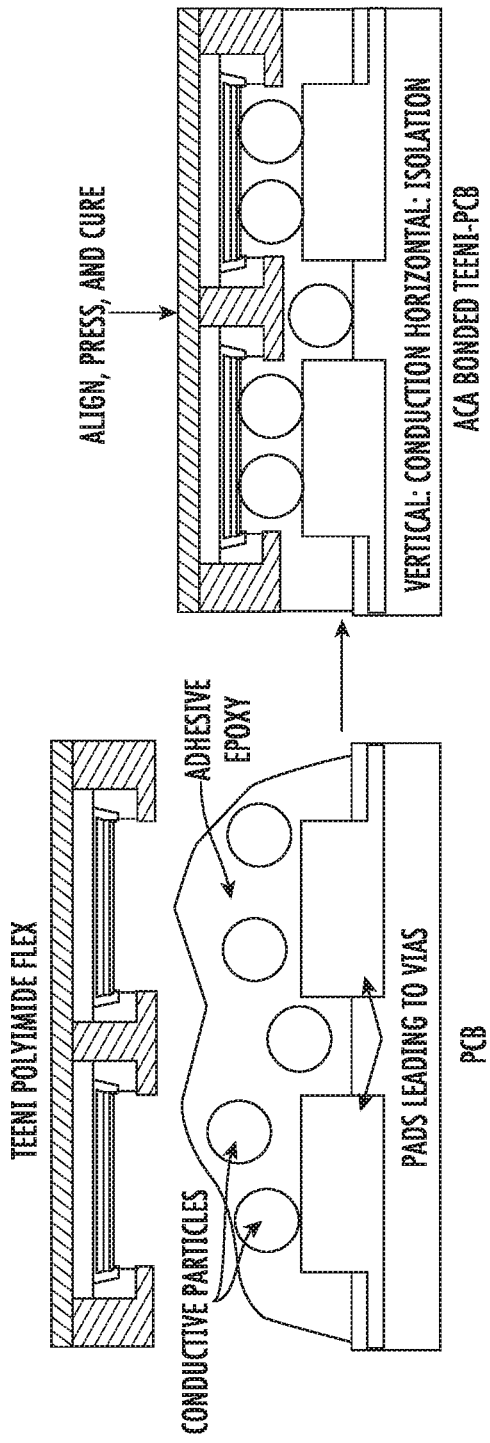
Figure 17B:
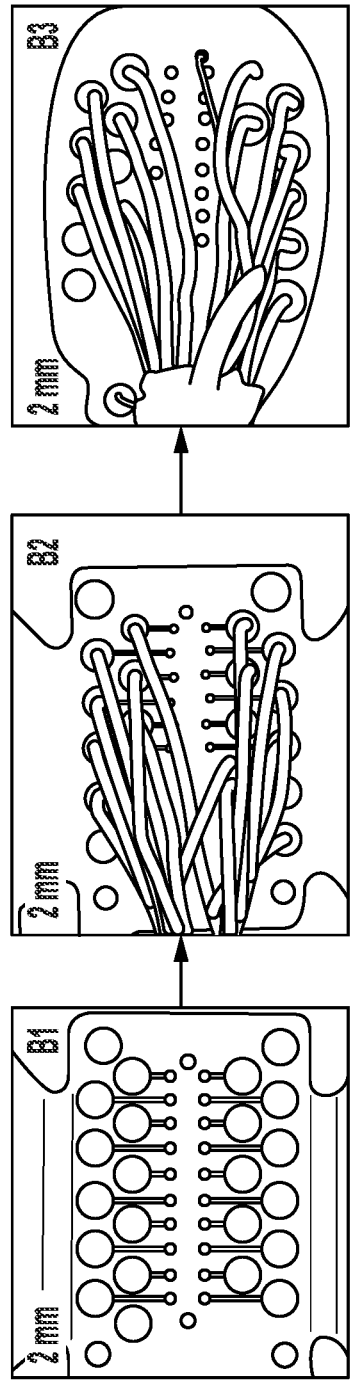
Figure 18:
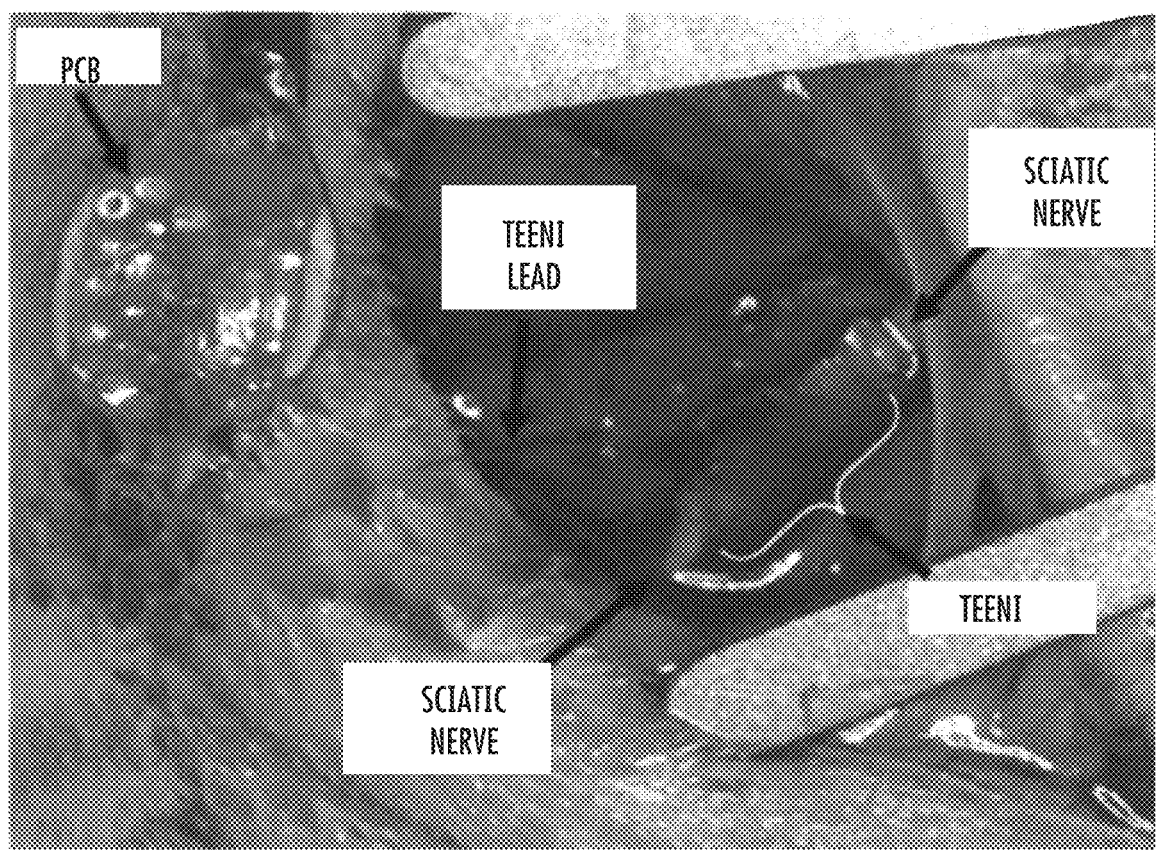
Figure 19:
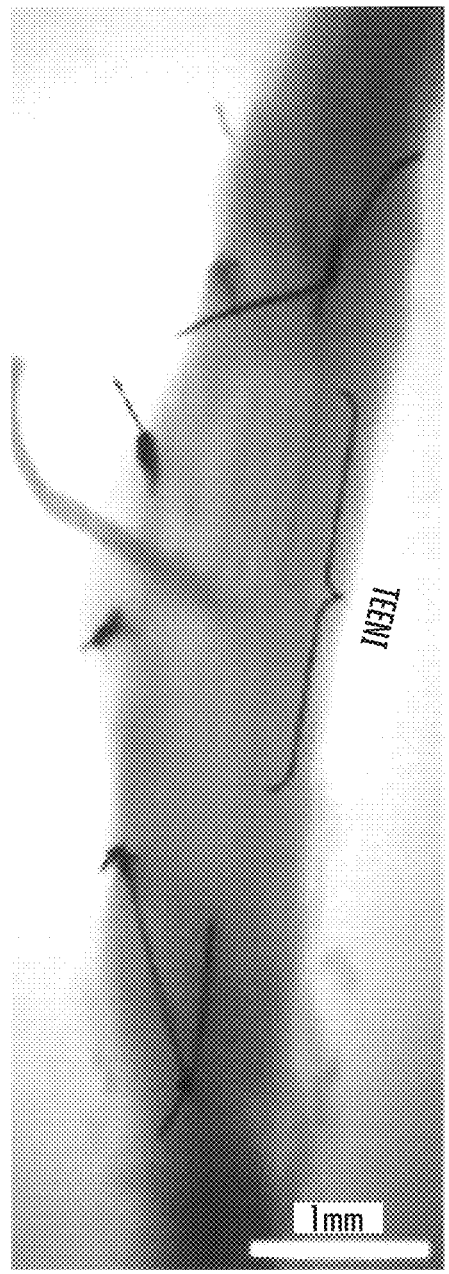
Figure 20A:
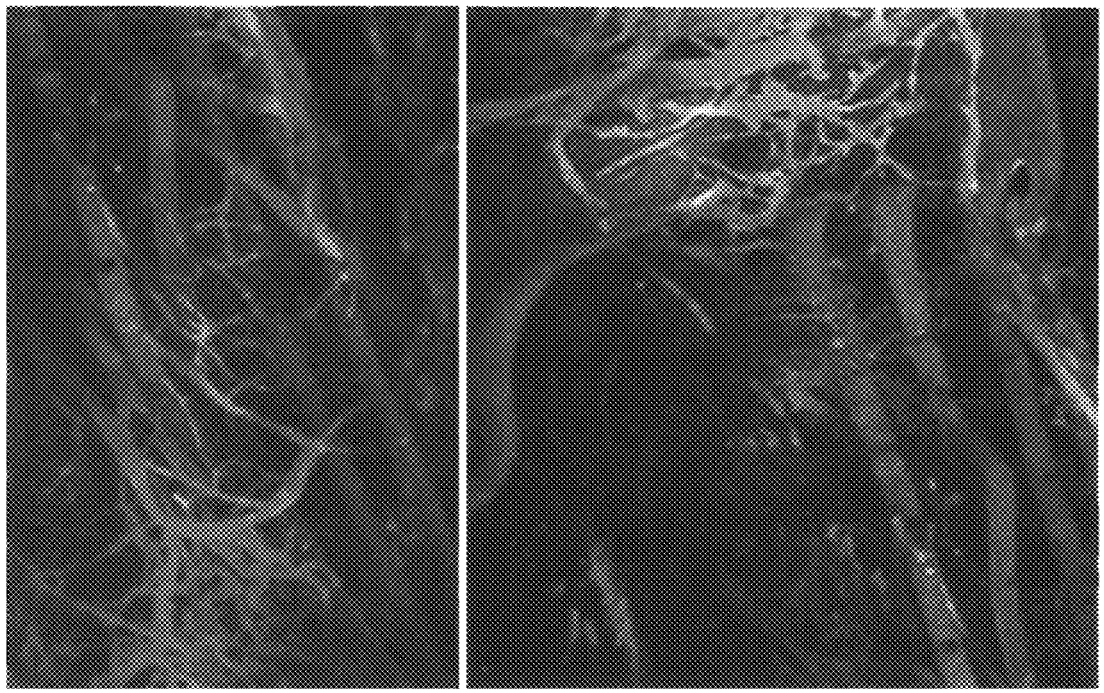
Figure 20B:
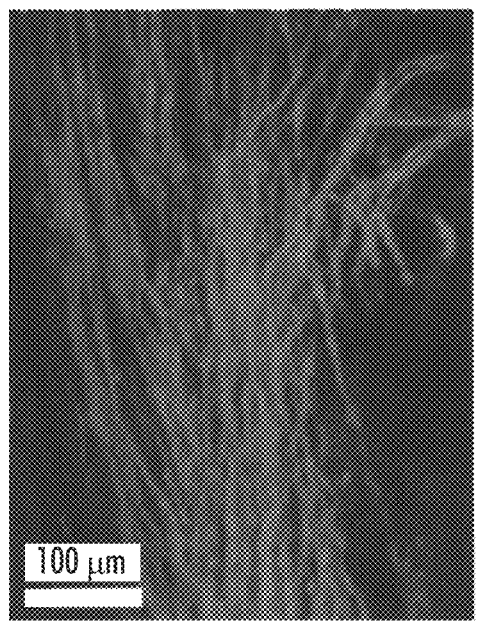
Figure 21B:
Figure 21D:
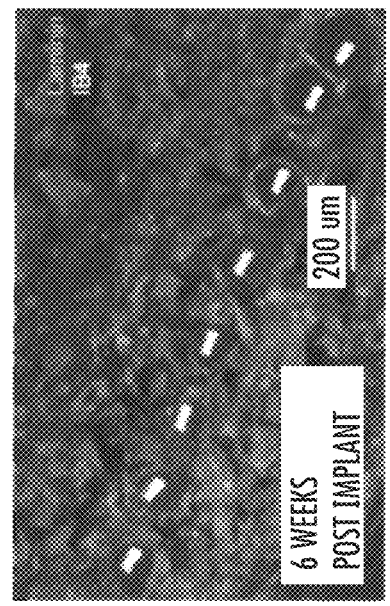
Figure 21A:
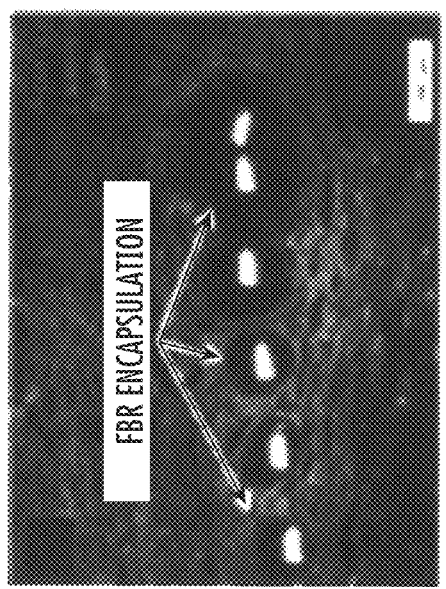
Figure 21C:
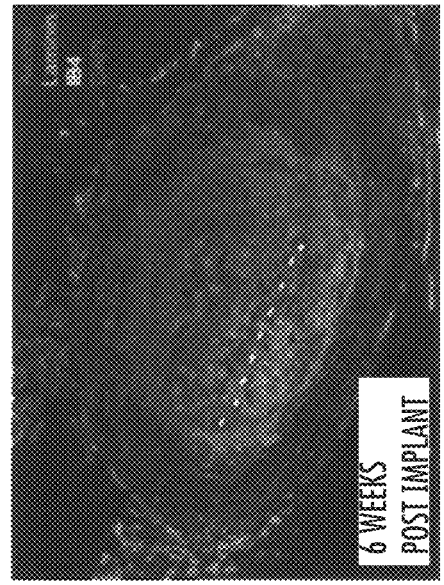
Figure 21E:
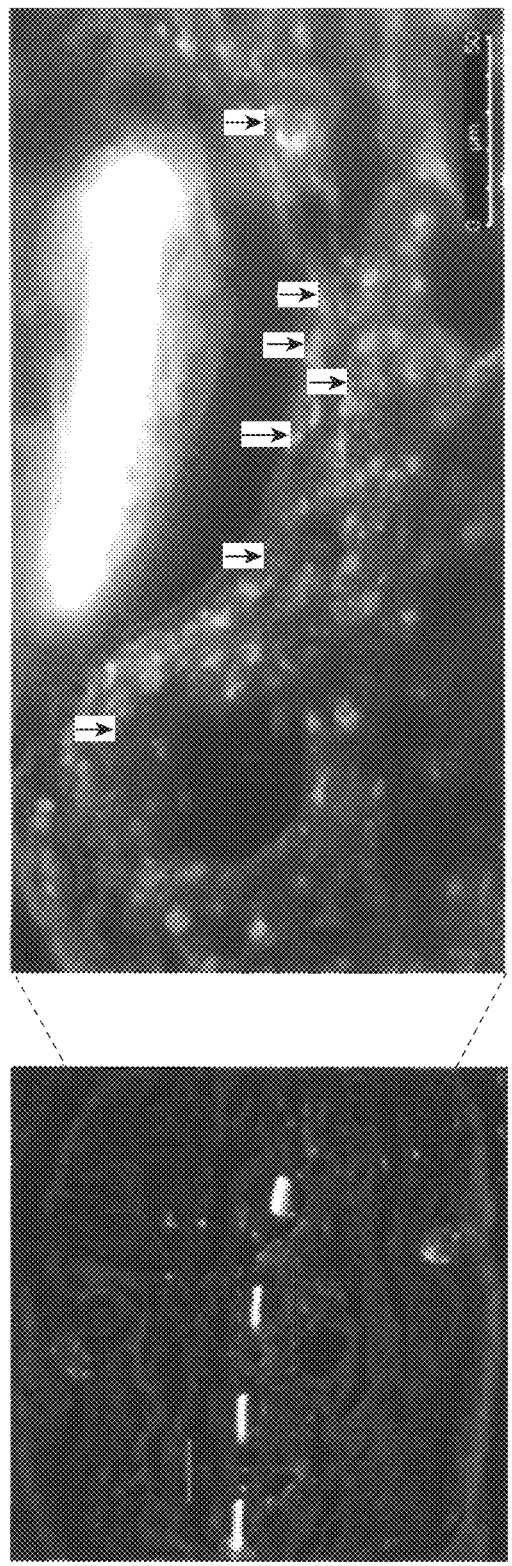
Figure 22:
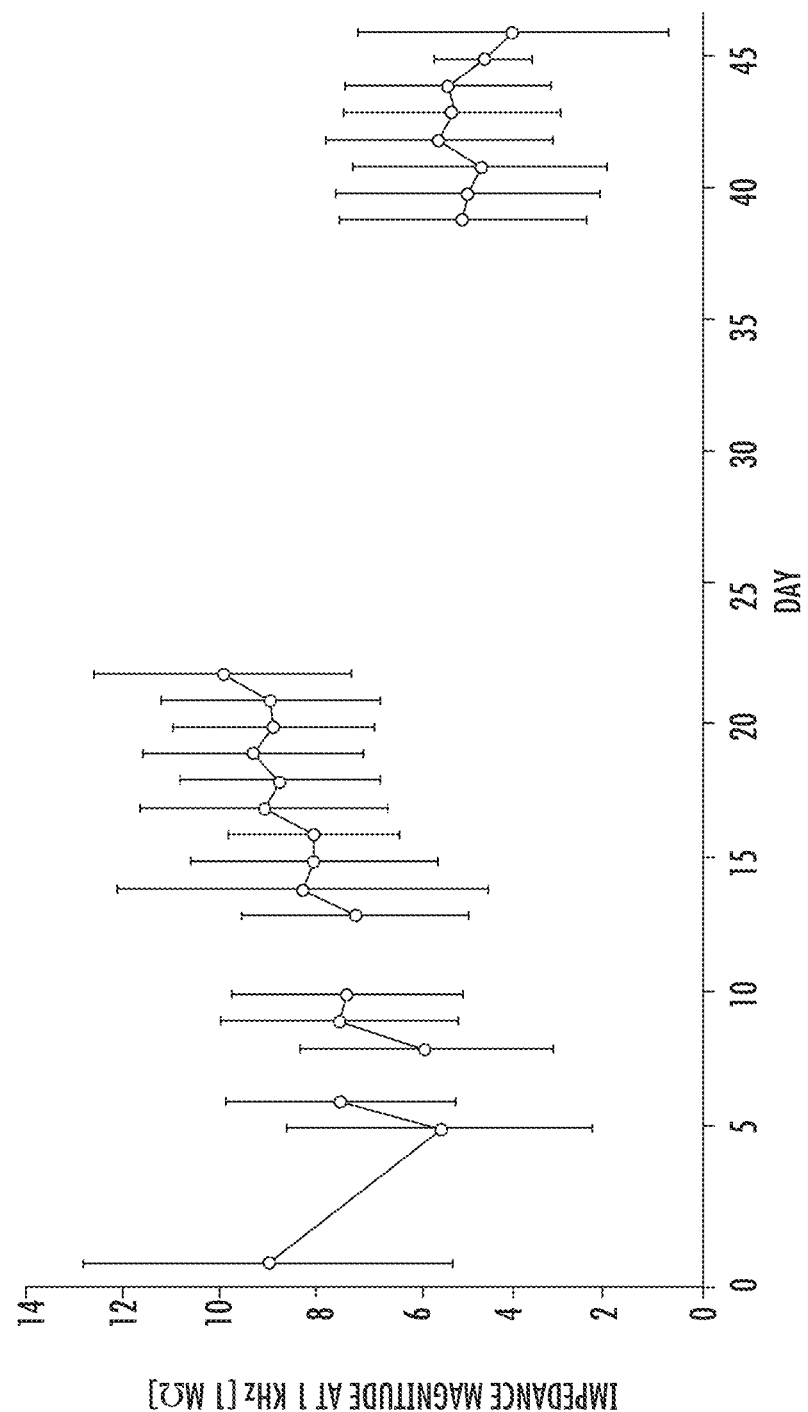
Figure 23:
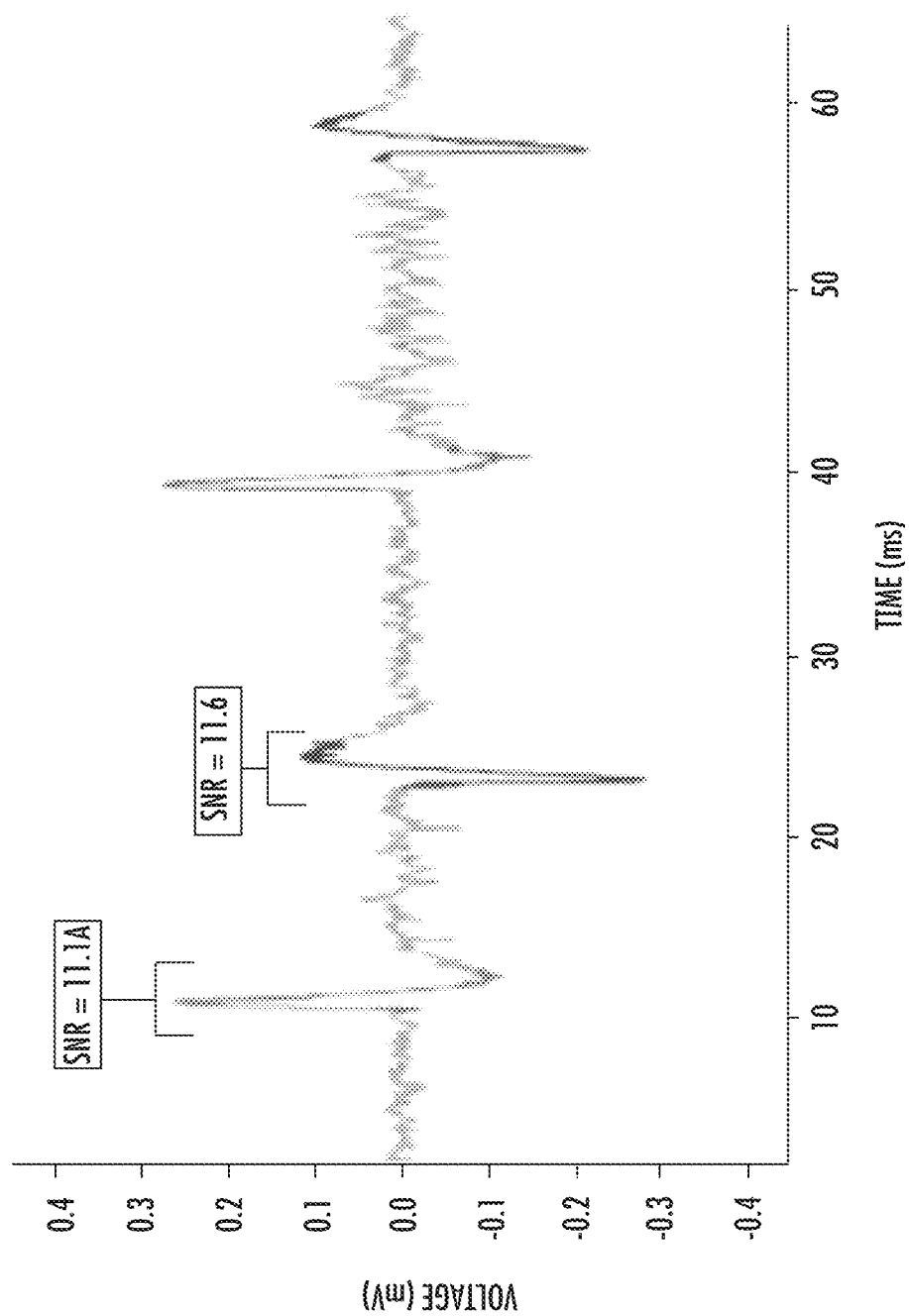
Figure 24:
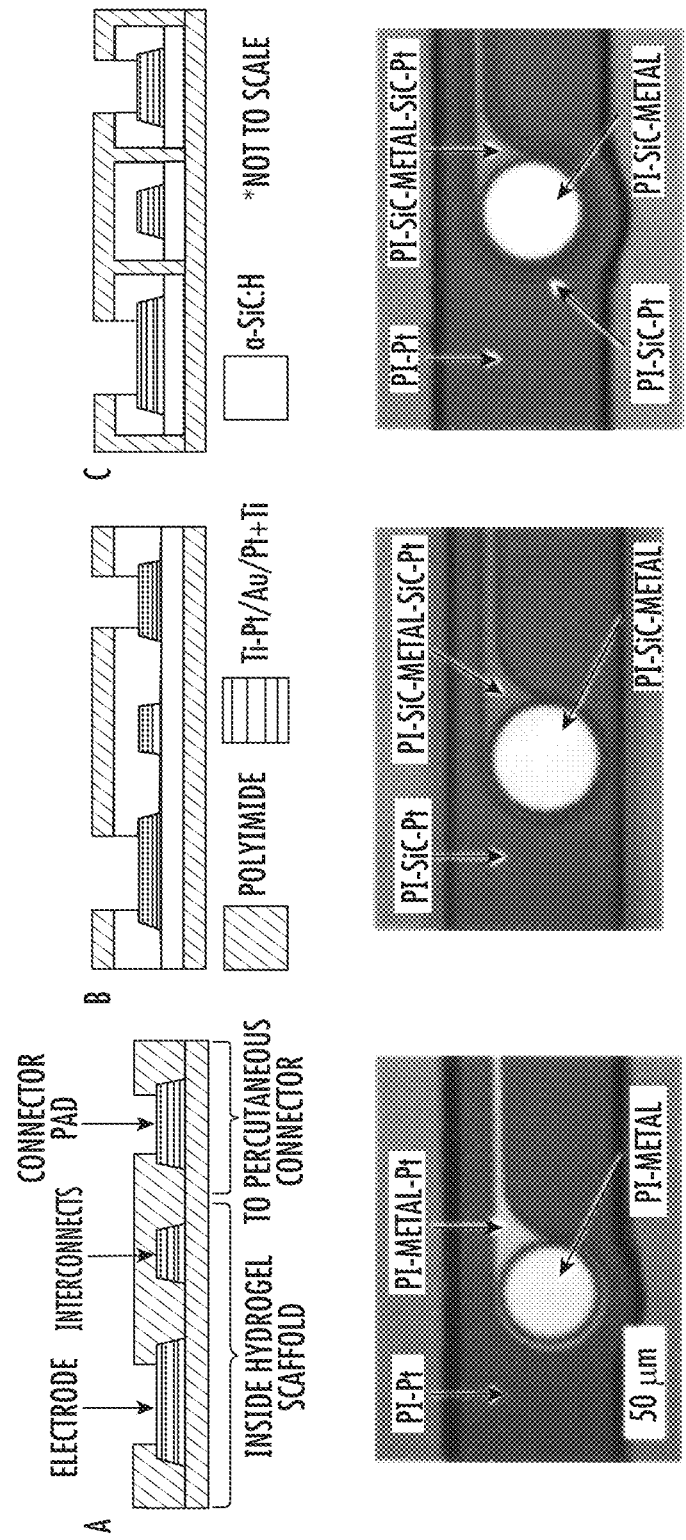
Figure 25:
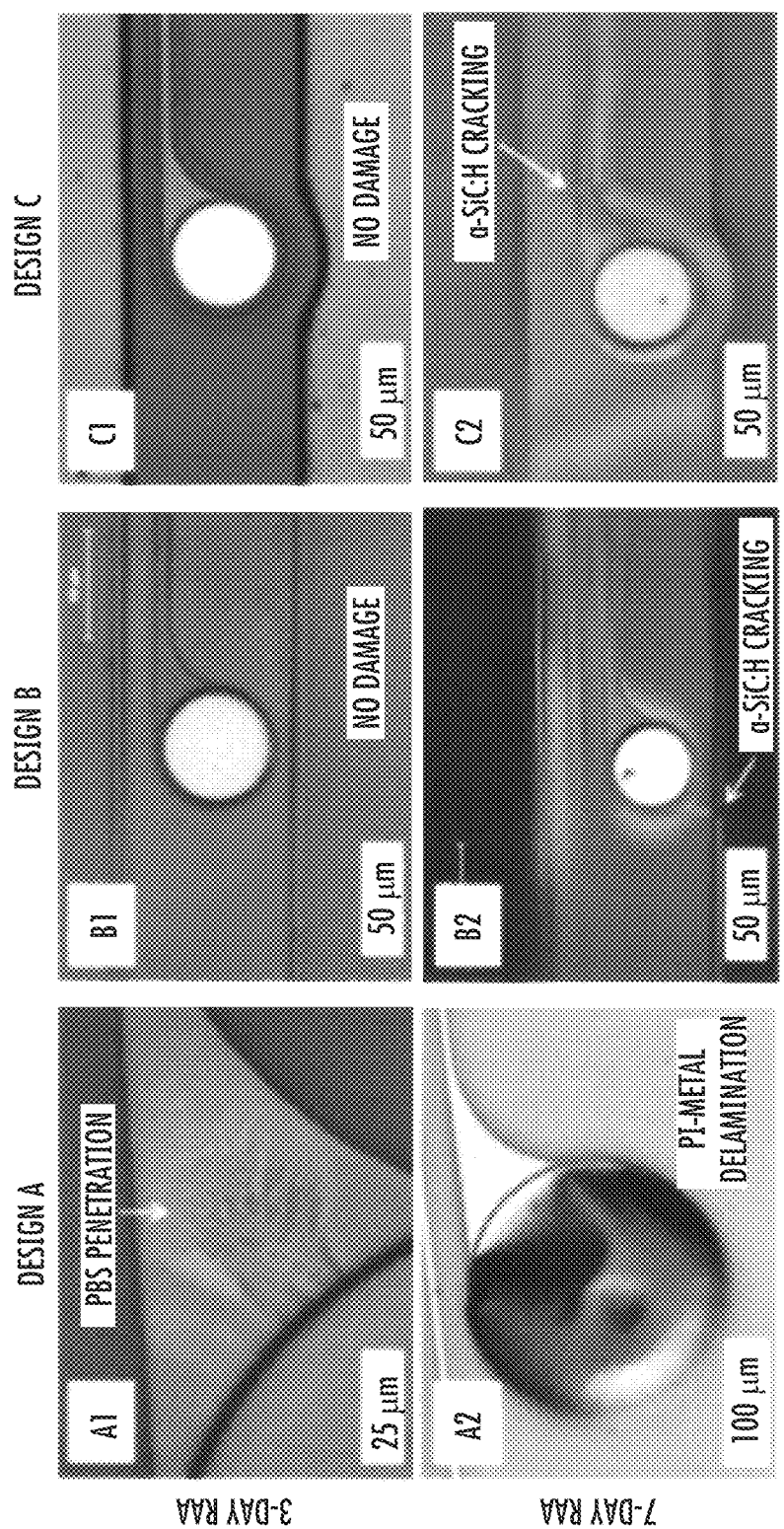
Figure 26:
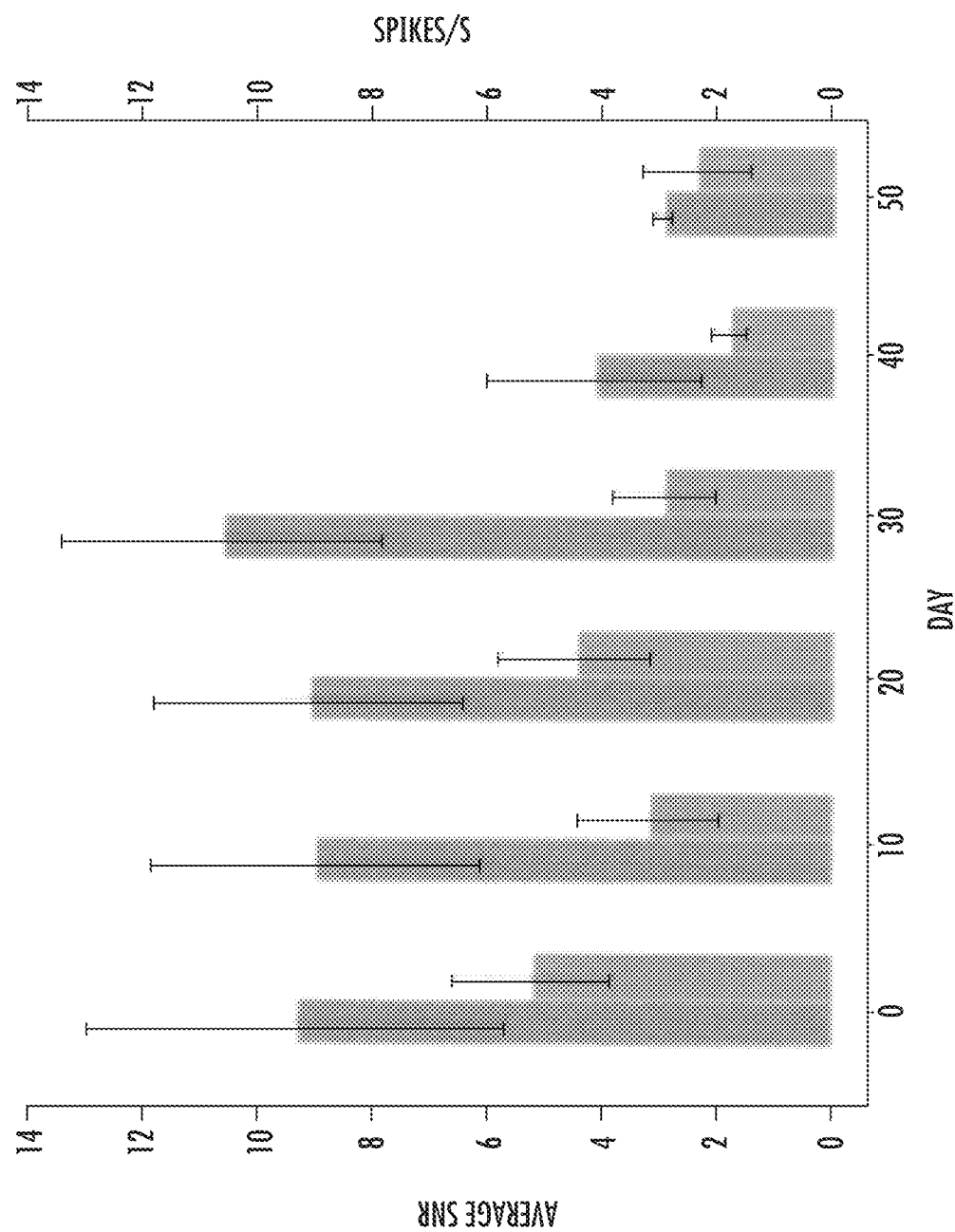
Figure 27:
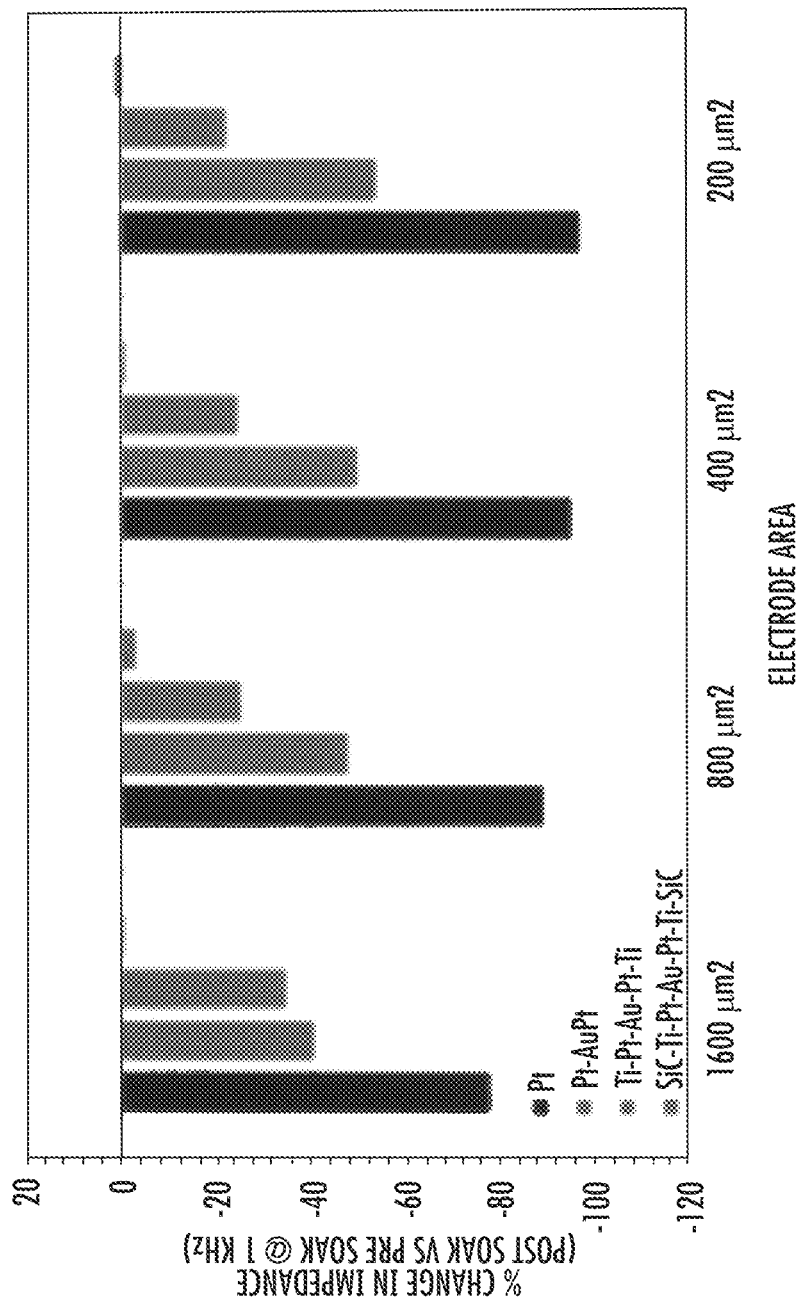
Figure 28:
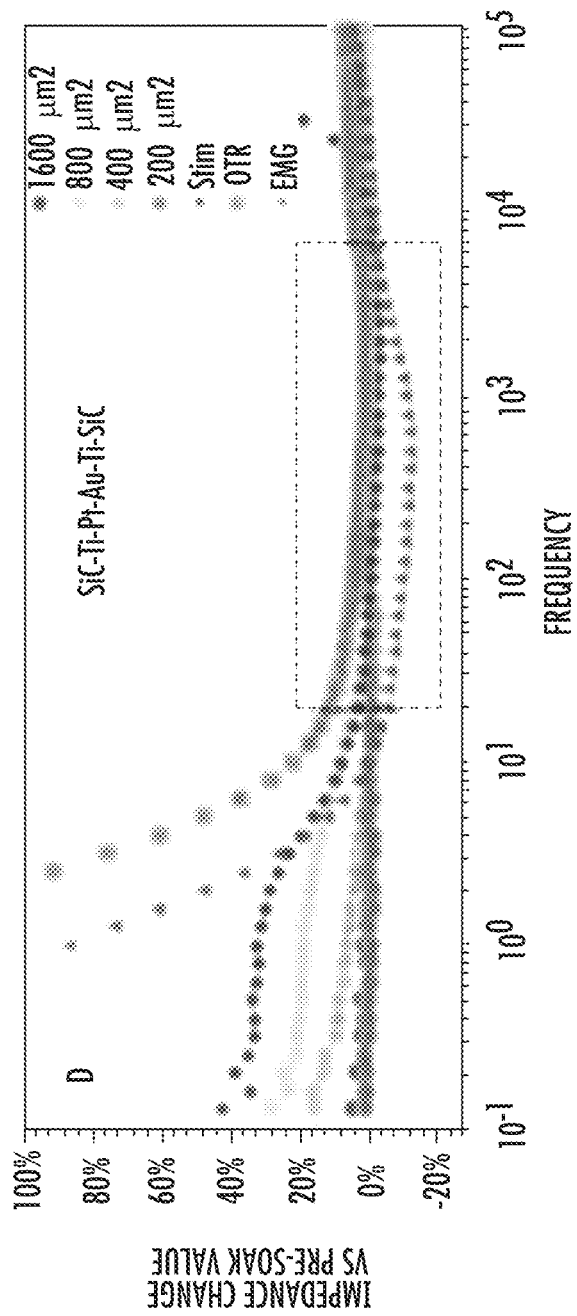
Figure 29A:
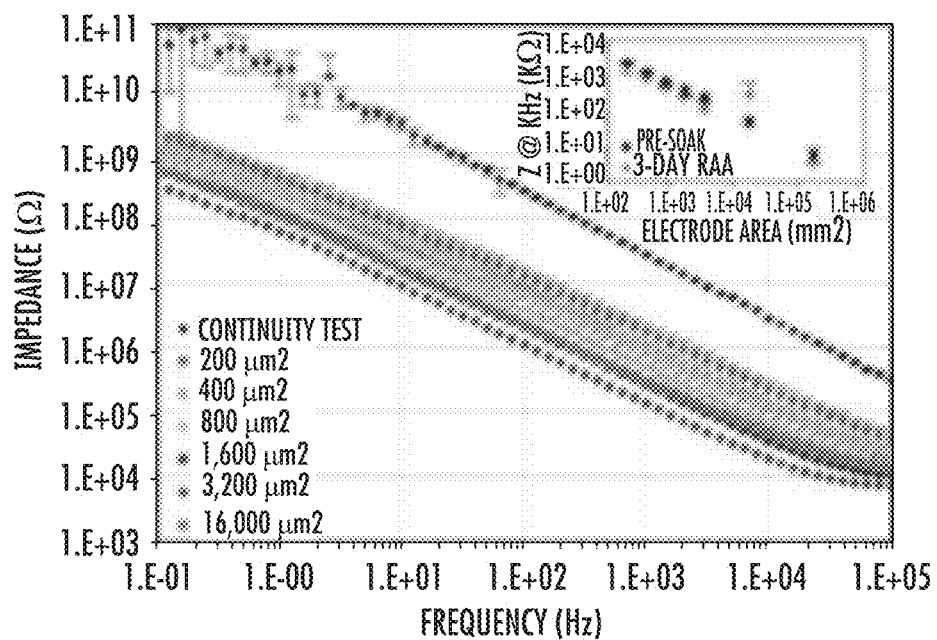
Figure 29B:
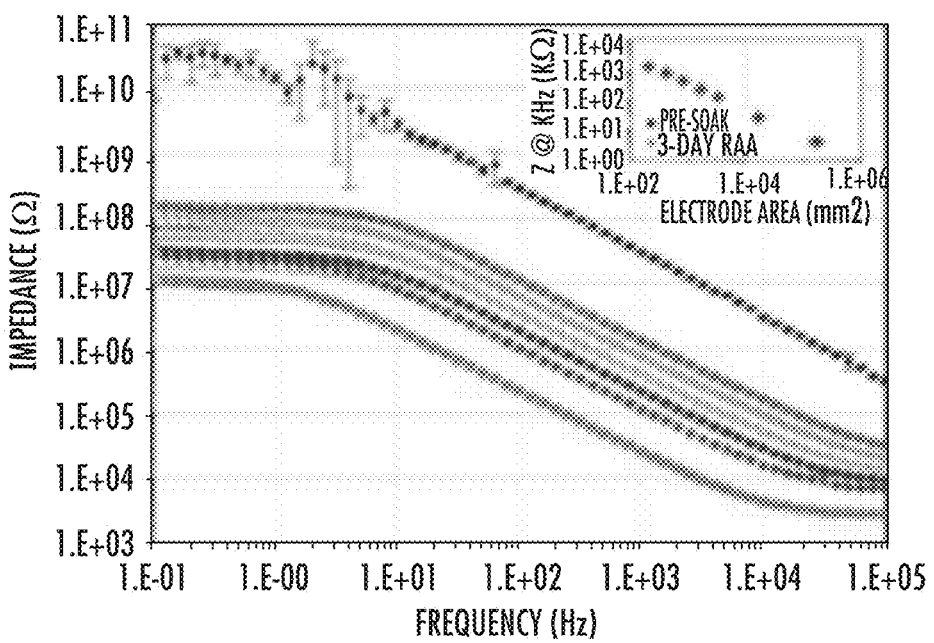
Figure 30:
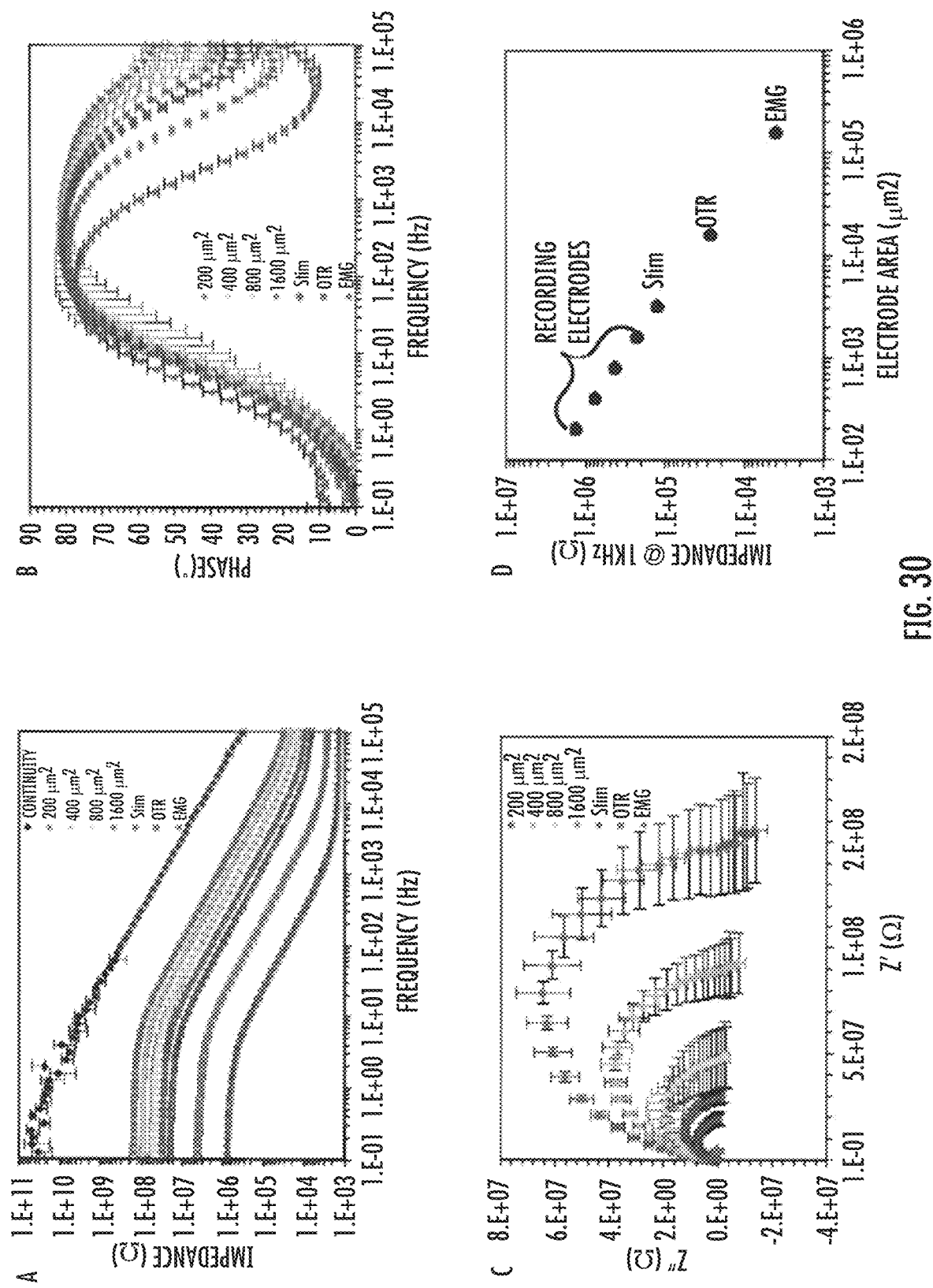
Figure 31:
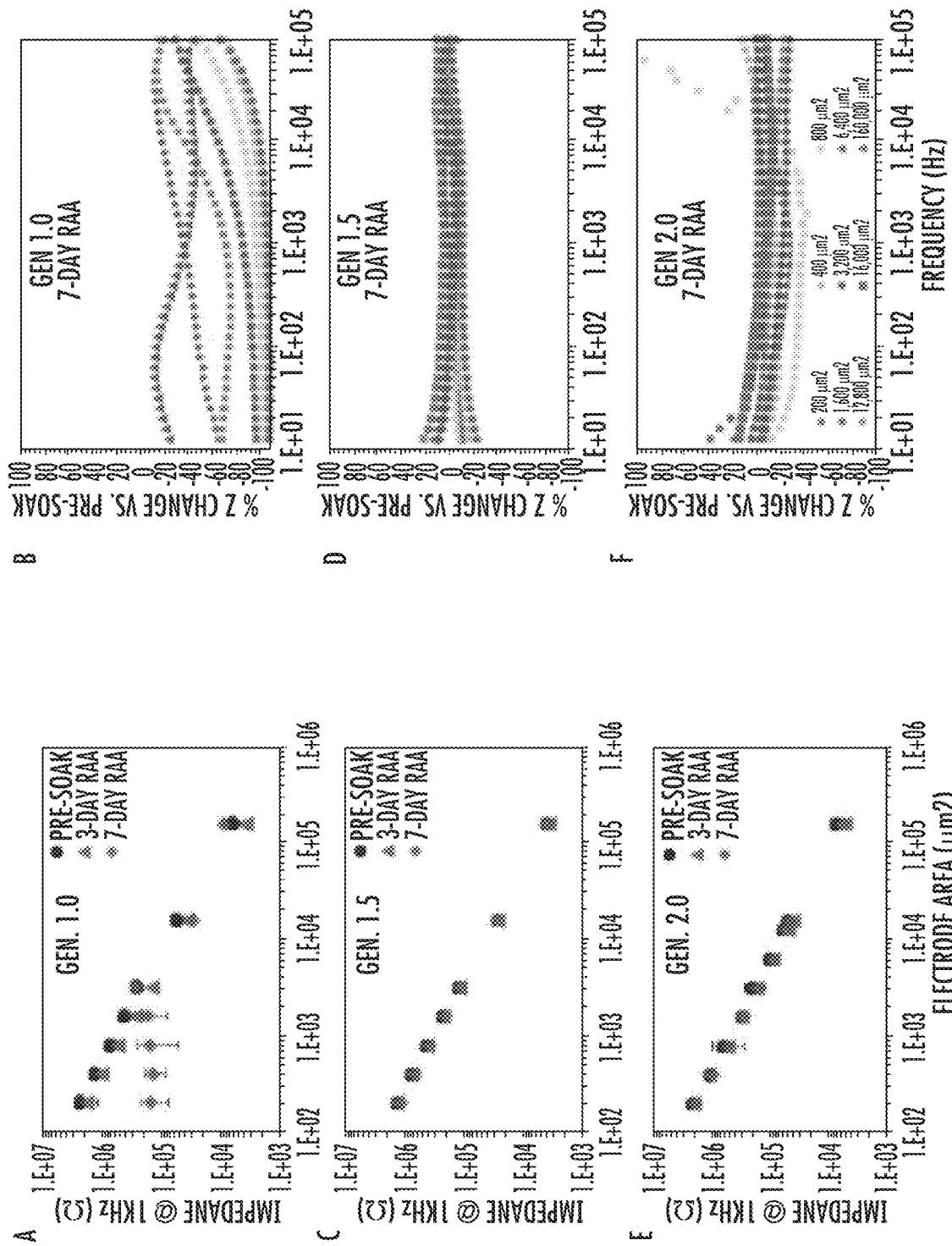

FIGS. 17A-B illustrate packaging for a TEENI device in accordance with certain embodiments of the invention;

FIG. 18 shows a system including a TEENI device implanted in a rat sciatic nerve transection in accordance with certain embodiments of the invention;

FIG. 19 is an optical microscope image of an explanted nerve that regenerated through a TEENI scaffold with the TEENI device visible inside the nerve in accordance with certain embodiments of the invention;

FIG. 20A is a lightsheet microscope image of a TEENI device and the vasculature inside a regenerated nerve in accordance with certain embodiments of the invention;

FIG. 20B shows regenerated axons within a TEENI device in accordance with certain embodiments of the invention;

FIGS. 21A-E show immuno-labeled cross-sections of an explanted TEENI device showing foreign body response encapsulation around the threads of the TEENI device in accordance with certain embodiments of the invention;

FIG. 22 is a plot of impedance magnitude of a TEENI device over time in accordance with certain embodiments of the invention;

FIG. 23 is a plot of electrophysiological recordings from a chronically implanted TEENI device in accordance with certain embodiments of the invention;

FIG. 24 shows cross-sections and images of three electrodes showing different adhesion layers and device designs used to test various abiotic failures of material interfaces in accordance with certain embodiments of the invention;

FIG. 25 shows optical images of the three electrodes of FIG. 24 after three days and seven days of reactive-accelerated-aging (RAA) soak tests in accordance with certain embodiments of the invention;

FIG. 26 is a plot of the signal-to-noise ratio (SNR) of single-unit action potentials and their firing rate versus implant duration in accordance with certain embodiments of the invention;

FIG. 27 is a plot of percent change in post-soak impedance relative to pre-soak values for different sized electrodes in accordance with certain embodiments of the invention;

FIG. 28 is a plot of change in impedance after an RAA soak test versus pre-soak impedance in accordance with certain embodiments of the invention;

FIGS. 29A-B are electrical impedance spectroscopy (EIS) Bode impedance spectra after a three day RAA soak test in accordance with certain embodiments of the invention;

FIG. 30 shows representative EIS data for TEENI microelectrodes in accordance with certain embodiments of the invention; and FIG. 31 shows representative EIS data for TEENI microelectrodes 33 after three days and seven days of reactive-accelerated-aging (RAA) soak tests in accordance with certain embodiments of the invention.

DETAILED DESCRIPTION

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

For upper-limb amputees, the peripheral nervous system is a promising target to interface with in order to control technologically sophisticated robotic limbs. Recent advances have shown that electrical stimulation of axons with peripheral-nerve interfaces can successfully provide natural multi-perception sensory feedback and alleviate phantom-limb pain in upper-limb amputees. In contrast, similar breakthroughs are yet to be achieved in the pursuit of extracting high-resolution and reliable movement-intent signals from peripheral nerves. To provide fine movement control and elicit distinct sensory percepts, a comprehensive bidirectional nerve-interface would need a large number of independent motor and sensory channels. However, existing interfacing approaches grossly under-sample the heterogeneous population of efferent and afferent axons in peripheral nerves. Another challenge of existing strategies arises from the mismatch between the elastic properties of native peripheral-nerve tissue (<100 MPa) and that of silicon-based microelectrodes (200 GPa). This mismatch is hypothesized to trigger an exaggerated foreign-body response to the electrodes that can negatively affect its functional longevity.

To solve these problems, the invention includes, according to certain embodiments, a tissue-engineered electronic peripheral nerve interface (TEENI) device. The TEENI device may include a biomaterial support member (also referred to herein as a "scaffold") in which one or more thread sets are enclosed and supported. The thread sets may comprise a plurality of spaced apart electronic leads that are encased within an insulating sheath. The electronic leads may include one or more electrodes that are configured to come into contact with regenerated nerve fibers. In some embodiments, for example, the one or more thread sets may be enveloped and held in position during implantation by the biomaterial support member. As explained in greater detail below, the material for the biomaterial support member is selected to provide mechanical properties that help reduce foreign-body response. In some embodiments, the support member may degrade and be replaced with regrown and maturing axons. In certain embodiments, for example, the support member may comprise a hydrogel-based scaffold. Advantageously, this approach may be scalable to be spread throughout a sizable volume using precisely arranged multiple thread sets. Single or multiple thread sets, as determined by the size and location of the target nerve, may be incorporated in the biomaterial support member to make the TEENI device implantable and functionally engage with a substantial portion of the peripheral nerve. In some embodiments the TEENI device may be configured to interface with peripheral nerves of varying sizes (i.e., from the centimeter scale down to approximately 100 µm) by using the appropriate number of thread sets required to spread throughout the needed volume of interaction. The TEENI approach may also provide ample room for axonal regeneration and maturation over time without space constriction. In this regard, the TEENI device may be configured to regenerate a transected nerve to form a regenerated nerve, detect and record neural activity in the regenerated nerve, and stimulate the regenerated nerve.

I. Definitions

As used herein, the term "axially spaced apart" means that the electronic leads are arranged so that they are spaced apart from each other along a central axis and that the spacing is substantially perpendicular relative to the central axis.

As used herein, the term "laterally spaced apart" means that the spacing is in the cross direction as opposed to the longitudinal direction.

As used herein, the term "biomaterial" refers to a material that is biodegradable and biocompatible. A biomaterial may be derived from natural or synthetic sources.

As used herein, the term "biocompatible" refers to a material that is derived from natural or synthetic sources, and that is capable being partially or fully implanted in intimate contact with tissue of a host organism. Biocompatible materials should elicit limited to no adverse biological response by the host organism. For example, biocompatible materials are characterized by limited or no carcinogenicity, immunogenicity, teratogenicity, and toxicity in the host organism.

As used herein, the term "biodegradable" refers to a material that is derived from natural or synthetic sources and that is capable of being degraded within the host organism. Following implantation, biodegradable materials should maintain their mechanical properties until the material is no longer required, at which point the material may be absorbed and excreted by the host organism.

As used herein, the term "biocommunication" refers to the state in which an electrode is capable of receiving and forwarding signals created and/or transmitted by a nerve fiber.

As used herein, the term "microchannels" refers to tubules or tube-like formations within a construct. The microchannels have a generally elongated and/or cylindrical shape, with a generally circular cross-section. It should be recognized, however, that other cross-sectional configurations are within the scope of the invention. The microchannels have an open (e.g., hollow or substantially hollow) interior (referred to herein as a "lumen") creating a via/conduit that forms a scaffold/template for the growth of cells/tissues and can also facilitate the movement of fluid, cells, and other materials within and/or through the construct. In certain embodiments, the microchannels may have a diameter in the micron range (e.g., 1-100 μm, including diameters from 5-20 μm, and diameters with an average of about 10 μm).

As used herein, the terms "substantial" or "substantially", unless otherwise directed, may encompass the whole amount as specified, according to certain embodiments of the invention, or largely but not the whole amount specified according to other embodiments of the invention, e.g., within 10% of the recited amount, such as within 9%, 8%, 7%, 6%, 5%, 4%, 3%, 2%, or 1% of the recited amount.

II. TEENI Device

Figure 1:
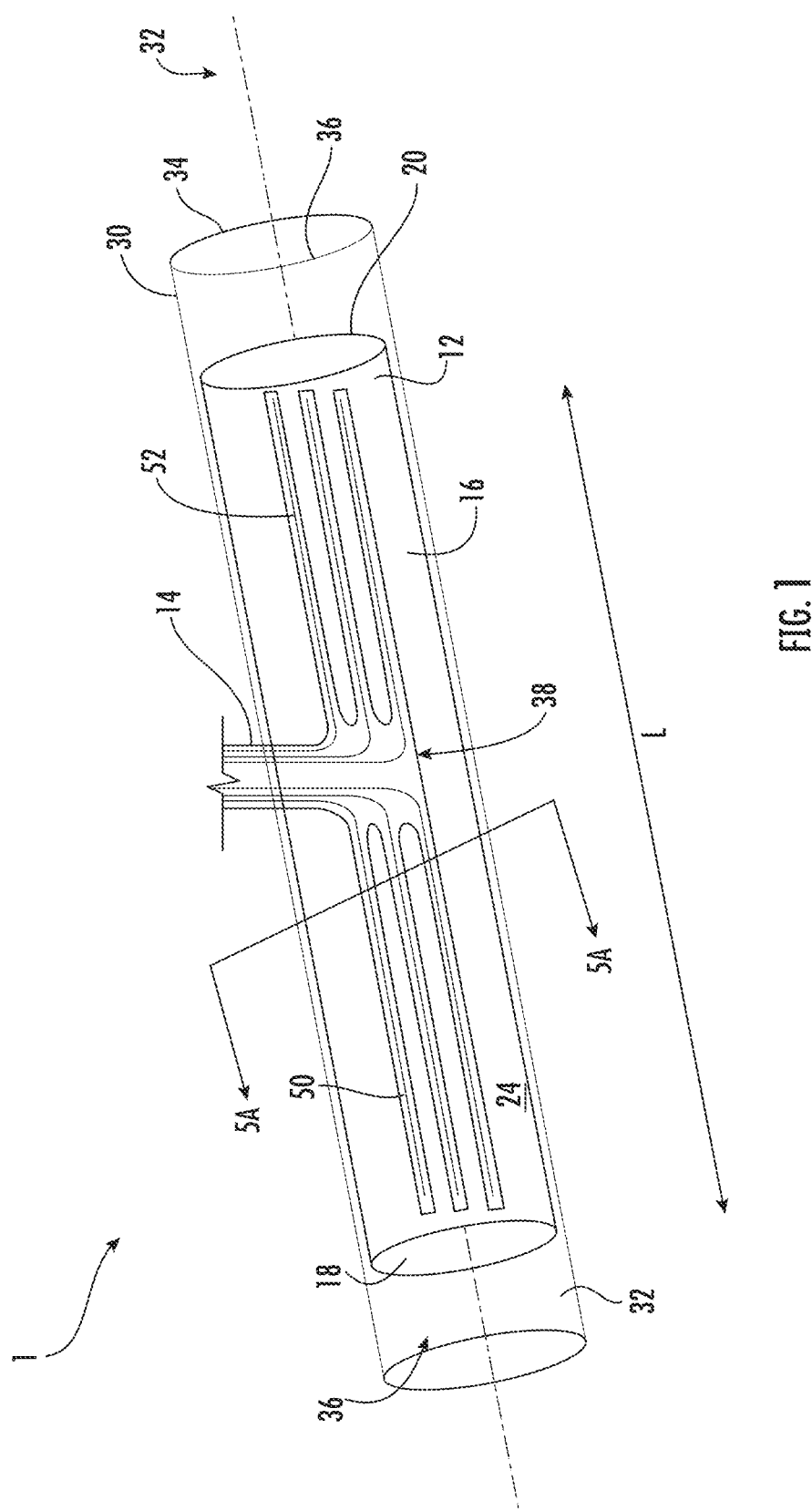
FIG. 1 illustrates a tissue-engineered electronic nerve interface (TEENI) device in accordance with certain embodiments of the invention.

With reference to FIG. 1, a tissue-engineered electronic nerve interface (TEENI) device in accordance with at least one embodiment of the invention is illustrated and broadly designated by reference character 1. As shown, the TEENI device 1 comprises a support member 12 having a length L in which at least one thread set 14 is disposed. As discussed below, each of the thread sets includes one or more arms that each may comprise a plurality of electronic leads having one or more electrodes that are configured to come into biocommunication with a portion of regenerated nerve fiber.

The support member 12 comprises a generally elongate body 16 having a proximal end 18 and a distal end 20, a central axis 22 extending therebetween, and an outer surface 24. In some embodiments, for example, the support member may comprise a hydrogel. In further embodiments, for instance, the hydrogel may comprise a biomaterial. In accordance with certain embodiments, for instance, the hydrogel may comprise a natural or synthetic biodegradable polymer. In this regard, the hydrogel may be resorbable by the body. The biodegradable polymer may be a thermoplastic polymer, a thermoset polymer, or any combination thereof. In some embodiments, for example, the thermoset polymer may be crosslinkable. In such embodiments, for instance, the thermoset polymer may be crosslinked using thermal energy and/or irradiation. Irradiation may include ultraviolet light, infrared radiation, microwave radiation, x-rays, electron beam radiation, proton or neutron beam radiation, or a combination thereof. The crosslinked materials can be highly crosslinked or lightly crosslinked in the form of hydrogels.

The biodegradable polymer may include one or more oligomers, homopolymers, a blend or oligomers and/or homopolymers, copolymers, ionomers, polyelectrolytes, dendrimers, or a combination thereof. Copolymers can include block copolymers, random copolymers, gradient copolymers, alternating copolymers, star block copolymers, or combinations thereof.

For example, the biodegradable polymer may comprise one or more polyacetals, polyolefins, polyacrylics, polycarbonates, polystyrenes, polyesters, polyamides, polyamideimides, polyarylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, styrene acrylonitrile, acrylonitrile-butadiene-styrene (ABS), polyethylene terephthalate, polybutylene terephthalate, polyurethane, ethylene propylene diene rubber (EPR), polytetrafluoroethylene, perfluoroelastomers, fluorinated ethylene propylene, perfluoroalkoxyethylene, polychlorotrifluoroethylene, polyvinylidene fluoride, polysiloxanes, or the like, or a combination thereof.

Examples of polyelectrolytes include polystyrene sulfonic acid, polyacrylic acid, pectin, carrageenan, alginates, carboxymethylcellulose, polyvinylpyrrolidone, or the like, or a combination thereof.

Examples of thermoset polymers include epoxy polymers, unsaturated polyester polymers, polyimide polymers, bismaleimide polymers, bismaleimide triazine polymers, cyanate ester polymers, vinyl polymers, benzoxazine polymers, benzocyclobutene polymers, acrylics, alkyds, phenol-formaldehyde polymers, novolacs, resoles, melamine-formaldehyde polymers, urea-formaldehyde polymers, hydroxymethylfurans, isocyanates, diallyl phthalate, triallyl cyanurate, triallyl isocyanurate, unsaturated polyesterimides, or the like, or a combination thereof.

Examples of blends of thermoplastic polymers include acrylonitrile-butadiene-styrene/nylon, polycarbonate/acrylonitrile-butadiene-styrene, acrylonitrile butadiene styrene/polyvinyl chloride, polyphenylene ether/polystyrene, polyphenylene ether/nylon, polysulfone/acrylonitrile-butadiene-styrene, polycarbonate/thermoplastic urethane, polycarbonate/polyethylene terephthalate, polycarbonate/polybutylene terephthalate, thermoplastic elastomer alloys, nylon/elastomers, polyester/elastomers, polyethylene terephthalate/polybutylene terephthalate, acetal/elastomer, styrene-maleic anhydride/acrylonitrile-butadiene-styrene, polyether etherketone/polyethersulfone, polyether etherketone/polyetherimide polyethylene/nylon, polyethylene/polyacetal, or the like.

According to certain embodiments, for example, the hydrogel may comprise at least one of collagen I, laminin, methacrylated hyaluronic acid (MAHA), glycidyl methacrylate-hyaluronic acid (GMHA), or any combination thereof. Additional descriptions of suitable hydrogels may be found in PCT/US2016/029122, U.S. Pat. No. 8,668,863, U.S. Pat. No. 8,946,194, U.S. Pat. No. 9,095,558, which are incorporated by reference herein.

Figure 16:
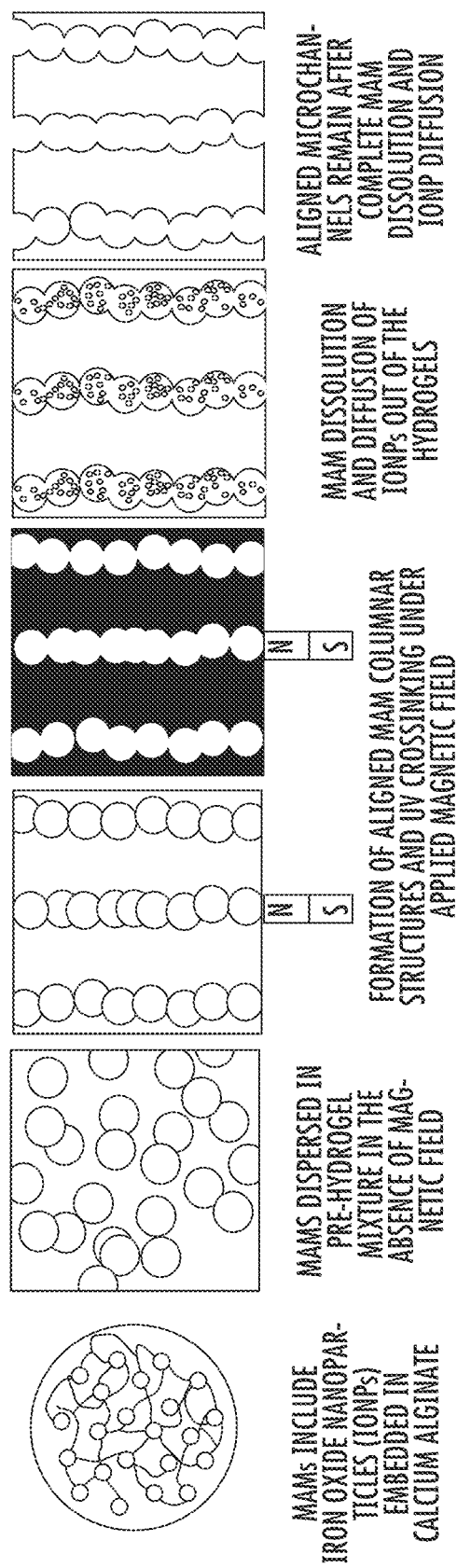
FIG. 16 illustrates the formation of magnetically templated aligned microchannels in accordance with certain embodiments of the invention.

In one embodiment, the support member 12 may be substantially solid with minimal void or porosity. In other embodiments, the support member 12 may be porous or at least partially porous. In further embodiments, and as shown in FIG. 16, the support member 12 may include a plurality of magnetically templated aligned microchannels, as described in U.S. patent application Ser. No. 15/573,270 incorporated by reference herein in its entirety. For example, as shown in FIG. 16, a magnetic field is applied to a mold containing a crosslinkable and/or polymerizable biocompatible precursor material (e.g. a biocompatible, polymerizable polymer, a crosslinkable or photopolymerizable hydrogel of naturally derived biomaterial, etc.) mixed with a plurality of sacrificial magnetic microparticles (e.g., microparticles of a sacrificial/dissolvable matrix material with encapsulated/embedded magnetic nanoparticles). The magnetic field causes the microparticles to align and form a plurality of lines/columns of adjacent microparticles, where the columns are also substantially aligned with each other (e.g., substantially oriented in the same direction, substantially parallel, etc.). After allowing the particles to align, while still applying the magnetic field or immediately after removal of the magnetic field, appropriate stimulus is applied to the crosslinkable/polymerizable biocompatible material to activate the crosslinking/polymerization of the material (e.g., application of UV light for photopolymerizable materials, addition of a chemical crosslinker, heat activation, etc.). Upon crosslinking/polymerizing of the material, the biocompatible material substantially solidifies (gel, solid/semi-solid) to form a three dimensional (3D) scaffold around the aligned microparticles. After formation of the scaffold, the matrix material of the microparticles is dissolved/sacrificed, and the dissolved material and the magnetic nanoparticles diffuse/leach out of the scaffold through the microchannels and pores left behind by the microparticles. A portion of the microchannels, a network of interconnected microchannels, or a combination thereof may extend the length L of the support member 12. In certain embodiments, the microchannels may have a diameter in the micron range (e.g., 1-100 µm, including diameters from 5-20 µm, and diameters with an average of about 10 µm). In this regard, the support member 12 may have a tubular microstructure that mimics that of natural nerve, including aligned, gap-spanning tubes with a diameter comparable to natural peripheral nerve (e.g., approximately 10 µm) embedded in a biocompatible matrix and obtained through methods that are compatible with incorporating chemical and biological cues.

Moreover, in certain embodiments, additional biomolecules (e.g., cells, proteins, carbohydrates, nucleic acids, etc.) may be included in the biocompatible scaffold material and/or matrix material of the microparticles, and all of the polymerizing/crosslinking/dissolution steps are carried out in biocompatible conditions that are non-toxic/non-harmful to any such biomolecules (e.g., they do not interfere with the intended purpose/activity of the biomolecules).

In the illustrated embodiment, the support member 12 has a generally cylindrical shape in which the elongate body is generally linear. It should be recognized that other shapes are possible depending on the desired application. For example, the elongate body may have a non-linear shape that may include one or more curves, such as convex or concave curves.

Figure 2:
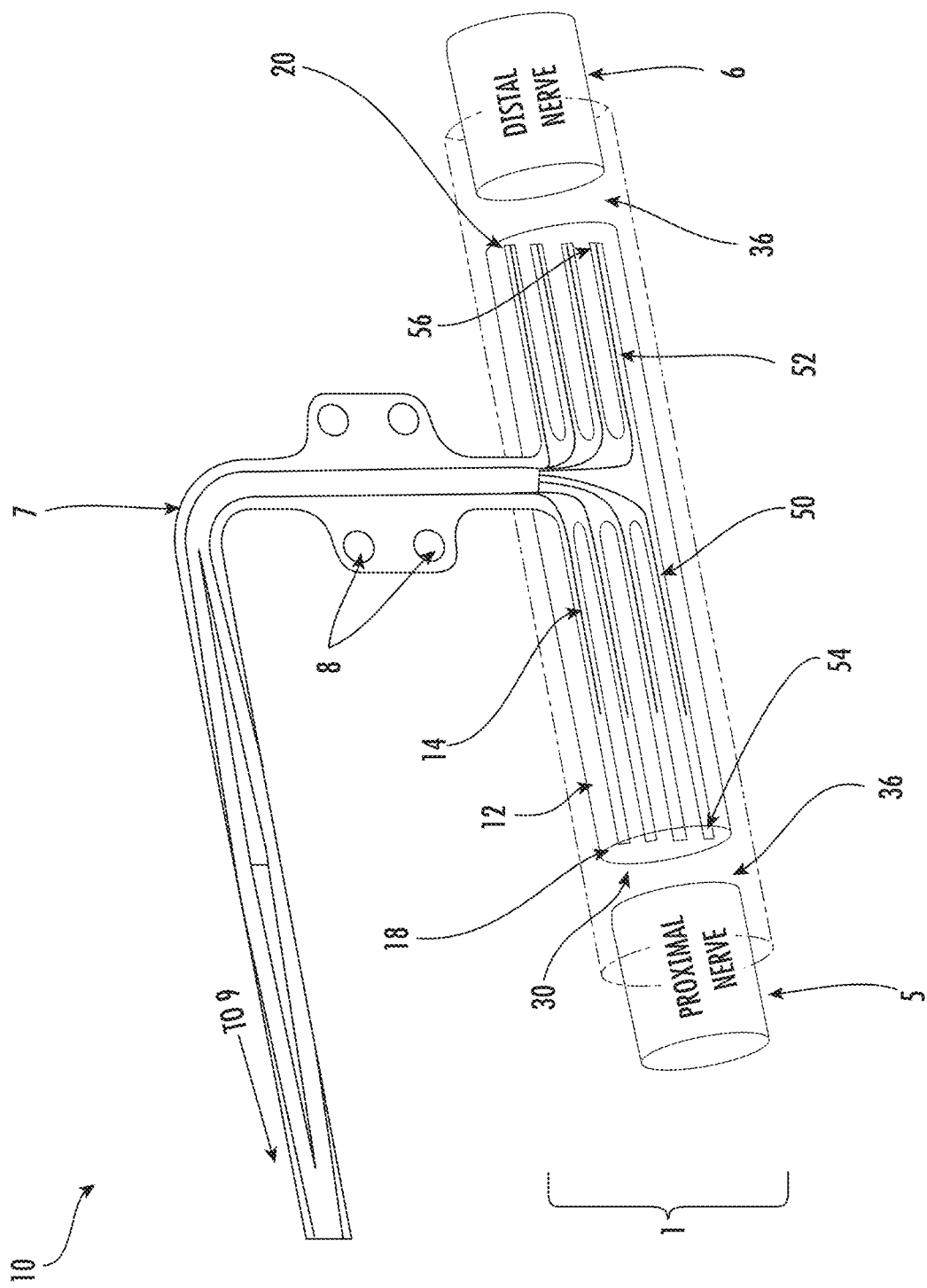
FIG. 2 illustrates a TEENI device attached to the ends of a transected nerve in accordance with certain embodiments of the invention.

In one embodiment, the support member 12 is surrounded by a sheath 30 that envelops and encloses the support member 12. In certain embodiments, for example, the sheath may comprise a proximal end portion 32 and a distal end portion 34. In the illustrated embodiments, the proximal and distal end portions 32, 34 extend beyond the proximal and distal ends 18, 20 of the support member 12. As shown in FIG. 2, the proximal and distal end portions each define a cavity or inner space 36 that is configured to receive a proximal or distal nerve end therein. The nerve fiber may be attached to the proximal and distal end portions of the sheath via suturing, an adhesive comprising a biomaterial, or a combination thereof.

Suitable materials for the insulating sheath may comprise any material that acts as a dielectric barrier, as understood by one of ordinary skill in the art. By way of example only, the insulating sheath may include at least one of a polyimide, a parylene, a liquid crystal polymer, silicon carbide, a diamond-like carbon film, a silicone, a polyurethane, or any combination thereof. In some embodiments, for instance, the insulating sheath comprises a biocompatible material. In further embodiments, for example, the sheath 30 may comprise a material that is biocompatible and biodegradable. Examples of materials for the sheath may include any bioresorbable material. In some embodiments, for instance, the sheath may comprise small intestinal submucosa (SIS).

In certain embodiments, the thread set includes one or more pairs of opposing arms (50, 52) in which each pair of arms extends longitudinally in a direction substantially parallel to the central axis. Each arm includes one or more electronic leads that are each in electronic communication with an electrode that is disposed towards a distal end of the arm. In one embodiment, the thread set 14 includes a central region 38 at which the arms come together and that extends outwardly from the outer surface 24 of support member. In certain embodiments, the central region of the thread set extends out from the support member proximate to a middle region of the support member.

Figure 3:
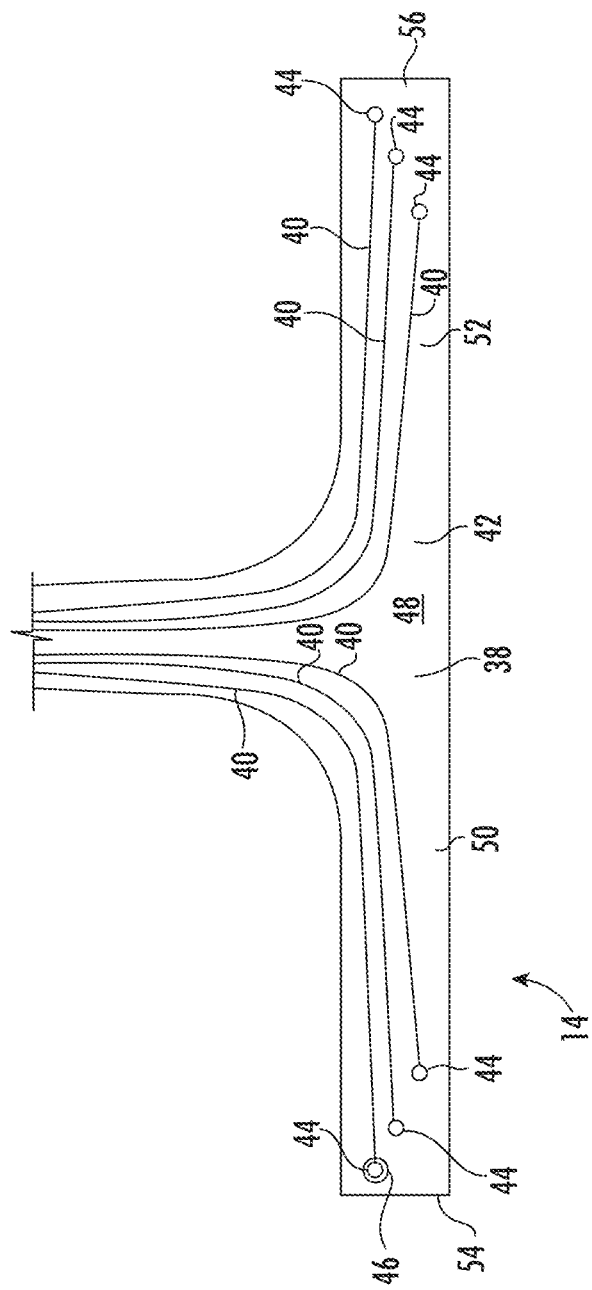
FIG. 3 illustrates a thread set of a TEENI device in accordance with certain embodiments of the invention.

With reference to FIG. 3, an example of a thread set 14 in accordance with at least one embodiment of the invention is illustrated. In one embodiment, the thread set comprises a plurality of electronic leads 40 that are spaced apart from each other and are enclosed within an insulating sheath 42. The electronic leads 40 comprise an electronically conductive material that is capable of receiving and transmitting electric signals between an electrode 44 and one or more circuits and/or electrical devices.

In certain embodiments, the outer surface 48 of the thread set 14 includes an opening 48 (represented by the dashed lines) formed therein in which a portion of the insulating sheath has been selectively removed to expose an electrode 44. During fiber regeneration, nerve fiber grows through the support member 12 and comes into contact with the exposed electrode to thereby bring the electrode and nerve fiber into biocommunication. The electrode may then communicate signals from the nerve fiber via the electronic lead to one or more circuits and/or electronic devices.

In the illustrated embodiment, each of the electronic leads are arranged axially in a spaced apart relationship from adjacent electronic leads 40. The illustrated embodiment shows a thread set having three pairs of electronic leads that extend in opposite directions from each other. It should be recognized that the thread set may include a single electronic lead or may include a plurality of electronic leads. For example, the number of leads may be from about 1 to 100, and in particular, from about 2 to 60, and more particularly, from about 6 to 40.

According to certain embodiments, for example, the electronic leads may comprise conductive metal traces, conductive polymers, or any combination thereof. By way of example only, the electronic leads may comprise platinum, gold, titanium, copper, poly(3,4-ethylenedioxythiophene) polystyrene sulfonate (PEDOT:PSS), polyaniline, and/or the like.

Figure 4:
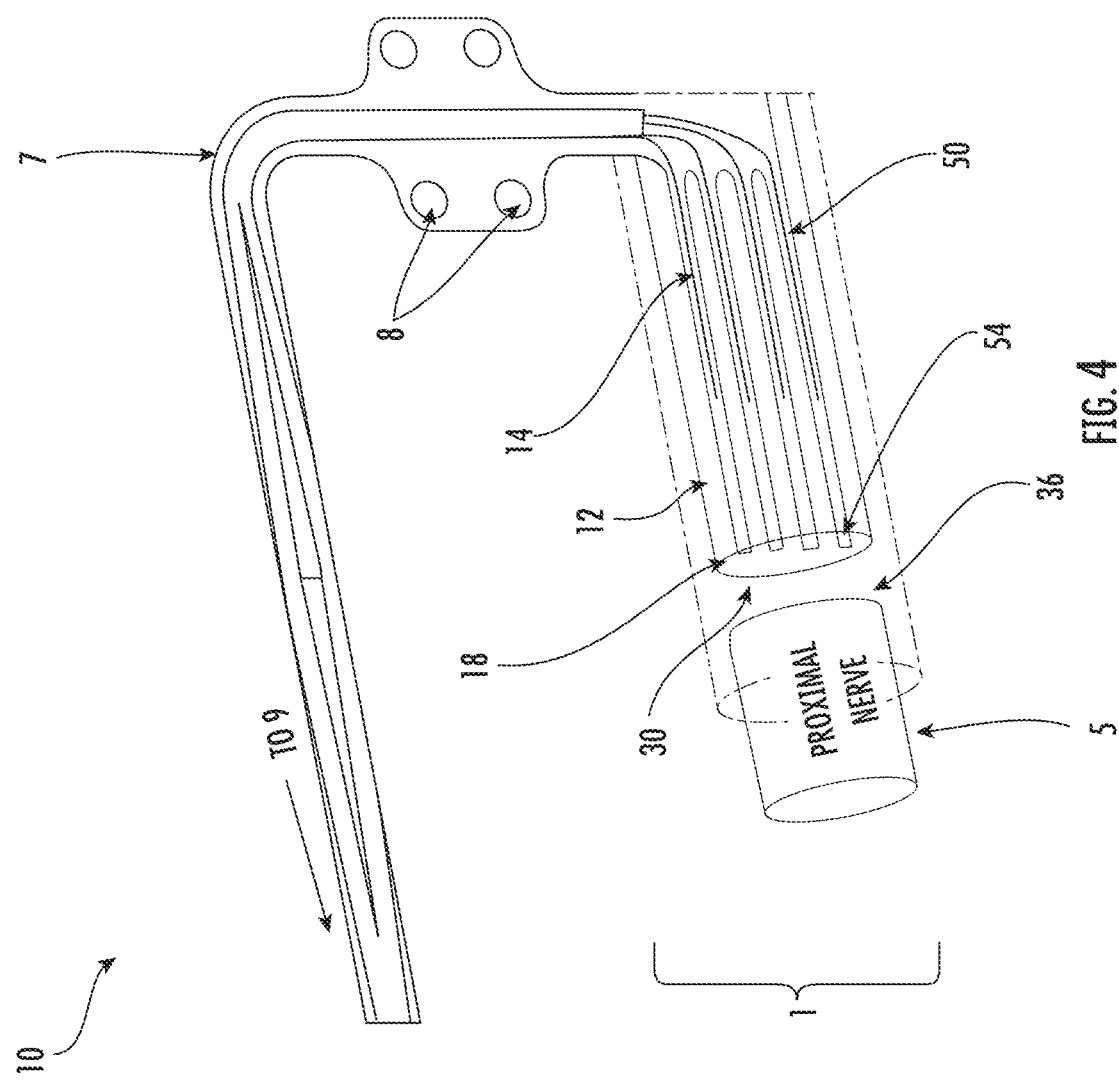
FIG. 4 illustrates a TEENI device attached to one end of a transected nerve in accordance with certain embodiments of the invention.

In one embodiment, the thread set 14 comprises a pair of opposing arms 50, 52 that extend in opposite directions relative to each other. In the illustrated embodiment, arm 50 includes a proximal end 54, and arm 52 includes a distal end 56. As can best be seen in FIG. 2, the proximal end of arm 50 extends towards the proximal end 18 of the biomaterial support member 12, and the distal end 56 or arm 52 extends towards the distal end 20 of the support member 12. In some embodiments, the thread set may include a single arm or plurality of arms that only extend in one direction. For example, the arms may only extend towards one of the proximal end 18 or the distal end 20 of the support member 12 (see, for example, FIG. 4, which illustrates a thread set having a plurality of arms that only extend towards the proximal end of the support member 12).

Figure 6:
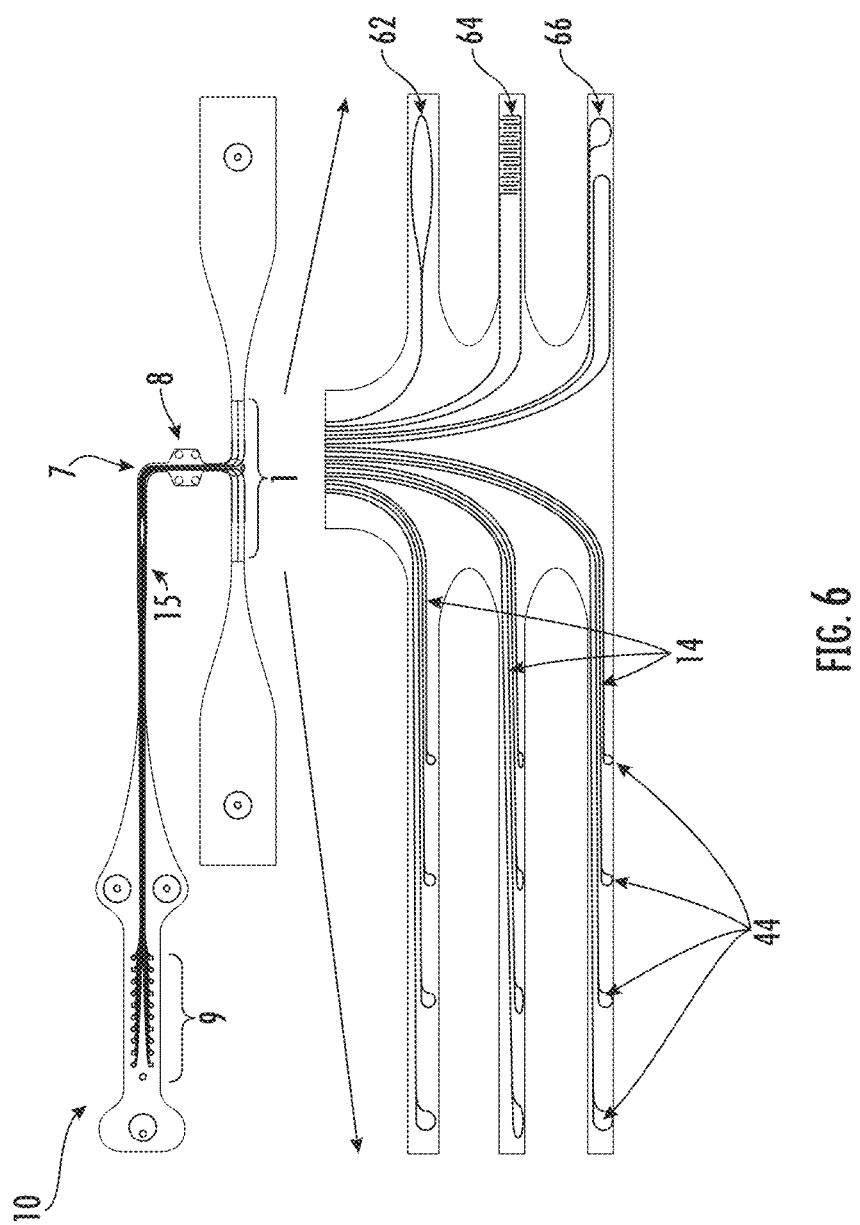
FIG. 6 illustrates a mask layout of a TEENI device in accordance with certain embodiments of the invention.
Figure 7:
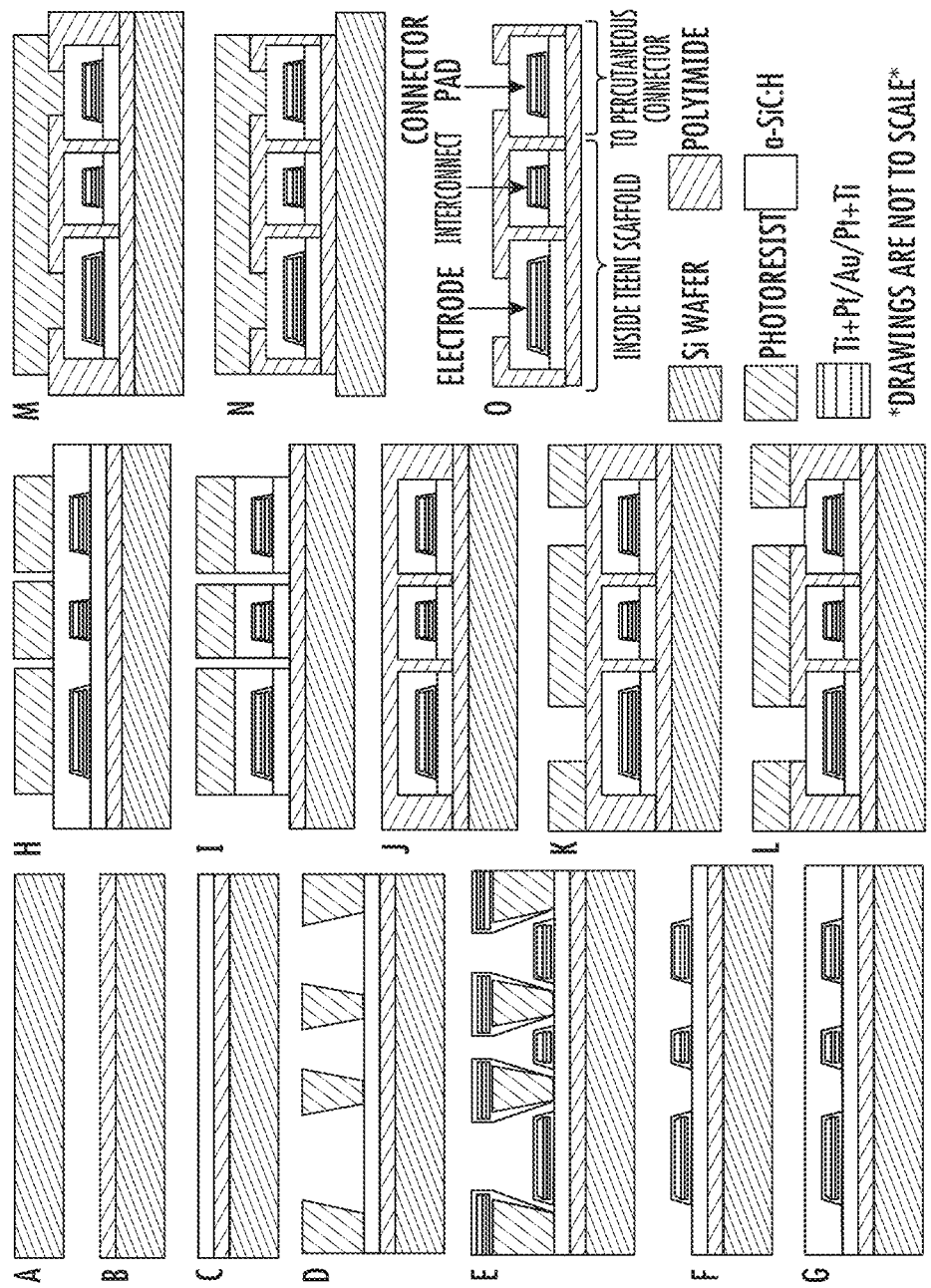
FIG. 7 illustrates the interface fabrication of a TEENI device in accordance with certain embodiments of the invention.
Figure 8B:
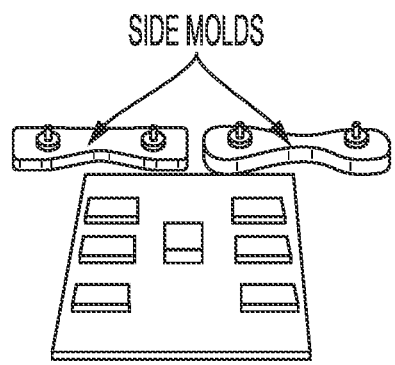
FIGS. 8A-8E illustrate an assembly process of a TEENI device in accordance with certain embodiments of the invention.
Figure 8A:
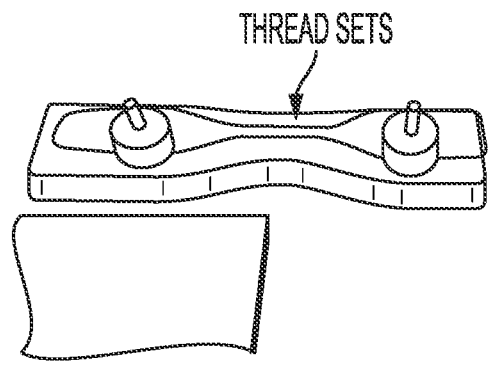
Figure 8C:
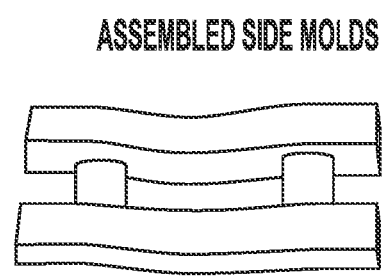
Figure 8D:
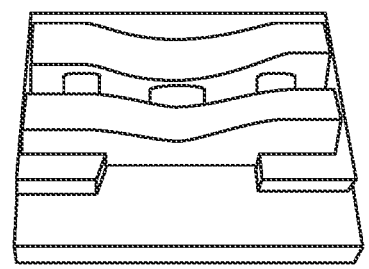
Figure 8E:
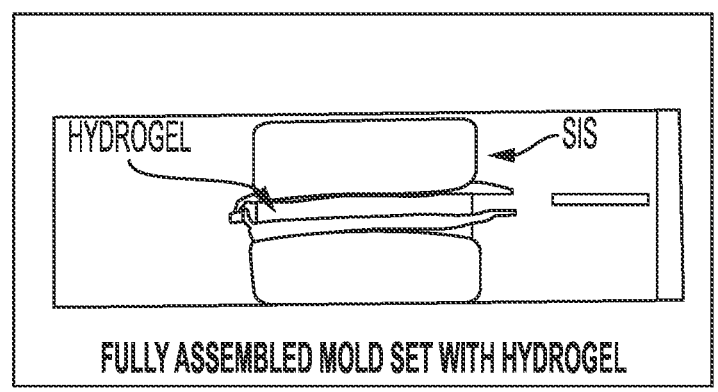
Figure 9:
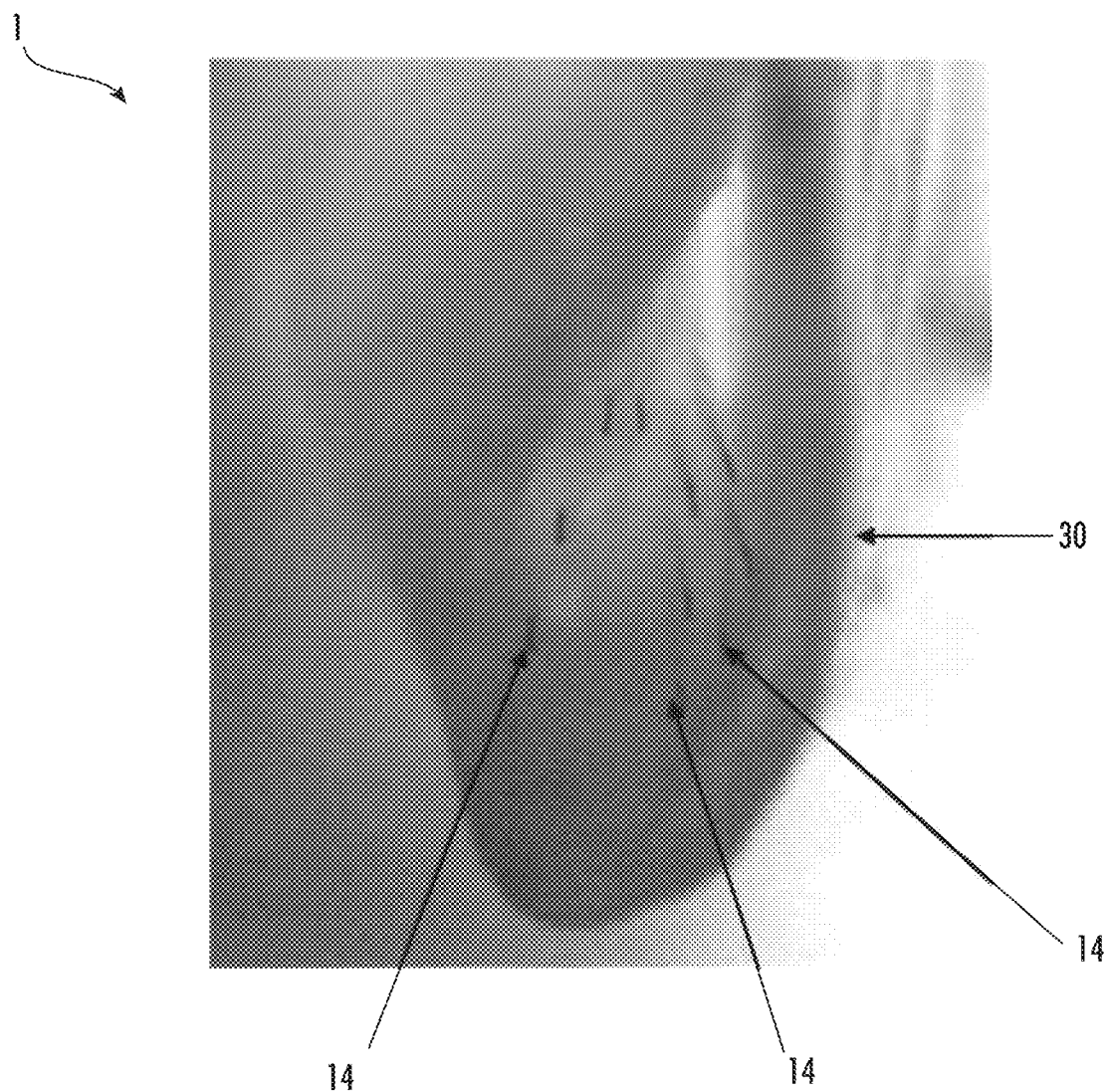
FIG. 9 is an image of a hydrogel support member having three TEENI thread sets in accordance with certain embodiments of the invention.

In some embodiments, the thread set 14 may include a plurality of pairs of arms that are arranged axially in a spaced apart relationship from each other. In this regard, FIG. 6 illustrates an embodiment in which the thread set includes 3 pairs of opposing arms in which each pair includes a proximal end and distal end. As shown in FIG. 6 and as briefly discussed above, the outer surface 48 of the thread set 14 may have portions of the insulating sheath selectively removed to expose a plurality of electrodes 44. In some embodiments, for example, the exposed electrode sites may comprise a different material from the electronic leads. For instance, the exposed electrode sites may comprise iridium, iridium oxide, PEDOT:PSS, platinum black, platinum grey, platinum, gold, polyaniline, platinum iridium, and/or the like. By way of example only, the exposed electrode sites on which the electrodes 44 may be placed may comprise a 300 nm thick stack of titanium+platinum/gold/platinum+titanium alternating layers in varying geometric surface areas, as shown in FIG. 7.

The plurality of electrodes 44 may comprise recording electrodes. Moreover, the TEENI device 1 may include an on-thread reference electrode 62, a dielectric integrity test structure 64, and/or an electrical continuity test structure and stimulation electrode 66. Such additional electrodes 62-66 may provide for assessment of dielectric integrity and electrical continuity of connecting leads in the thread set. These "house-keeping" test-structures may enable evaluation of the reliability of the TEENI device in vivo and separate identification of abiotic and biotic causes of electrode-failures should they occur. As further shown in FIG. 6, connecting element 7 may also include an EMG reference electrode 15 so that signals from muscles surrounding the nerve may be captured and used to attenuate unwanted EMG contamination.

Figure 5A:
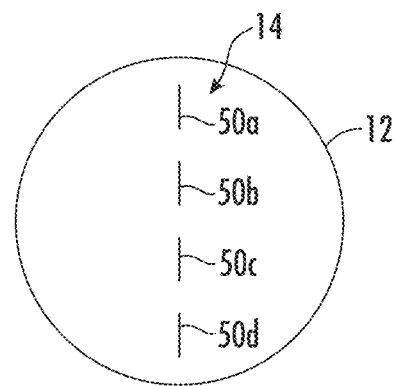
FIGS. 5A-5B illustrate cross-sections of support members of a TEENI device in accordance with certain embodiments of the invention.
Figure 5B:
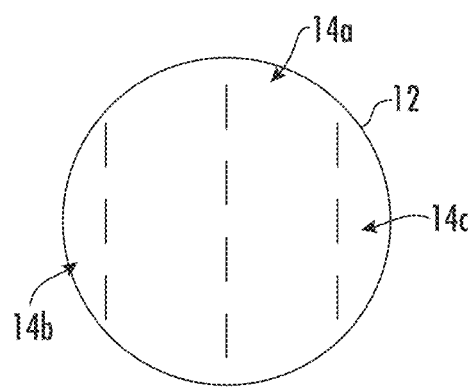

In some embodiments, the TEENI device may include a plurality of individual thread sets. In this regard, FIG. 5A illustrates a cross-section of the biomaterial support member 12 having a single thread set taken along line 5A of FIG. 1. As can be seen in FIG. 5A, the thread set includes a single thread set 14 having a plurality of axially spaced apart arms (50a, 50b, 50c, and 50d) that each may include a plurality of electronic leads. FIG. 5B on the other hand illustrates a cross section of the support member 12 comprising a plurality of thread sets (14a, 14b, 14c) that are laterally spaced across the width of the support member. In FIG. 5B, the TEENI device 10 includes three separate thread sets. In particular, the TEENI device of FIG. 5B includes two thread sets (14b, 14c) that each include three pairs of arms, and one thread set (14a) that includes four pairs of arms. The TEENI device of FIG. 5B comprises a 3-4-3 thread set arrangement. FIG. 6, for example, is an image of a support member comprising three TEENI thread sets in accordance with certain embodiments of the invention.

According to certain embodiments, the arms (or threads) of the thread set may be very small and may not occupy much space, both due to the size constraints imposed by peripheral nerves and to mitigate the foreign body response, which may lead to damaging inflammation and fibrotic tissue encapsulation. For example, in some embodiments, each arm (or thread) may have a length from about 1 mm to about 10 mm depending on the intended recipient of the TEENI device (e.g., human, rat, etc.). In further embodiments, for instance, each arm (or thread) may have a width from about 1 µm to about 1000 µm (e.g., about 10 µm to about 80 µm) and a thickness from about 1 µm to about 100 µm (e.g., about 1 µm to about 10 µm) depending on the intended recipient of the TEENI device (e.g., human, rat, etc.). In particular, in certain embodiments, each arm (or thread) may have a width of about 10 µm and a thickness of about 1.5 µm to protect the arm (or thread) from the foreign body response. Moreover, in some embodiments, the arms may be spaced apart by approximately 0 µm to about 1000 µm (e.g., about 40 µm to about 160 µm), depending on their individual widths and thicknesses.

Moreover, when the TEENI device is implanted (or sutured) into a subject in need thereof, the thread set arms (and the thread sets themselves in multi-thread set TEENI devices) may be evenly distributed through a volume of the transected nerve (e.g., proximal nerve 5 of FIG. 3) equal to the diameter of the transected nerve multiplied by a distance between one or more nodes of Ranvier.

FIG. 3 further illustrates portions of system 10, described in more detail below. In particular, as shown in FIG. 3, system 10 may include connecting element 7. Connecting element 7 may comprise a plurality of electronic leads connected to TEENI device 1 and extending to control element 9 (not shown). Further, connecting element 7 may include several suture holes 8. Suture holes 8 may be used to suture thread set 14 to the sheath 30 to provide additional positional stability during surgical handling, to sustain flexural stresses post-implantation, and/or the like.

II. System for Supporting a Transected Nerve

Figure 14:
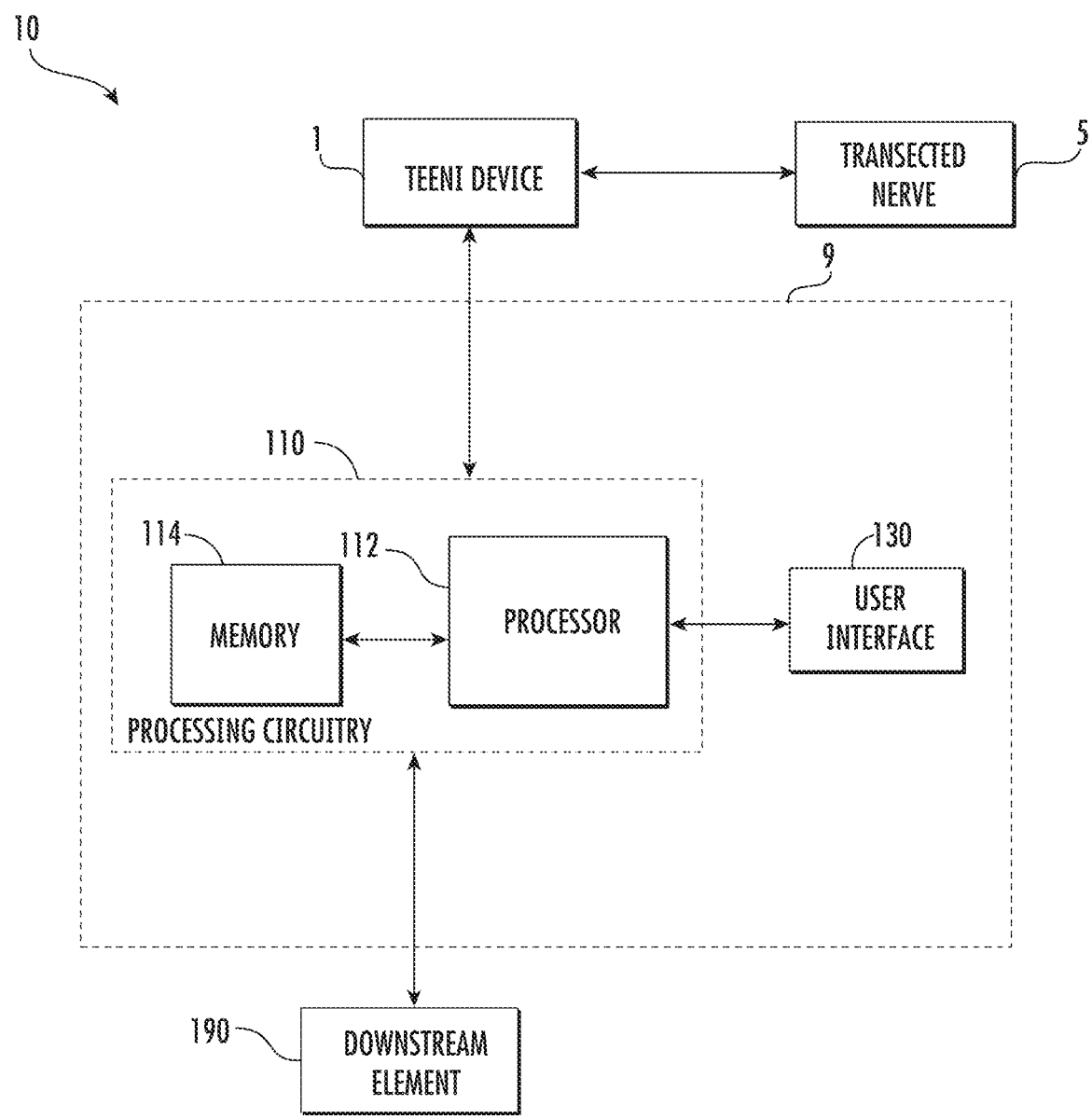
FIG. 14 is a block diagram of a system for supporting a transected nerve in accordance with certain embodiments of the invention.

In another aspect, a system for supporting a transected nerve is provided. The system includes the TEENI device 1 discussed above, a control element 9 having a user interface 130, and a downstream element 190. In some embodiments, for instance, the control element 9 may comprise a printed circuit board (PCB) or flexible printed circuit (FPC). For example, FIG. 14 is a block diagram of a system 10 for supporting a transected nerve 5 in accordance with certain embodiments of the invention. As shown in FIG. 14, the control element 9 of system 10 may include processing circuitry 110 that may be configured to interface with, control, or otherwise coordinate the operations of various components or modules described herein in connection with supporting a transected nerve as described herein.

In some embodiments, the processing circuitry 110 may be embodied as a chip or chip set. In other words, the processing circuitry 110 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The processing circuitry 110 may therefore, in some cases, be configured to implement an embodiment of the present invention on a single chip or as a single "system on a chip." As such, in some cases, a chip or chipset may constitute means for performing one or more operations for providing the functionalities described herein.

According to certain embodiments, the processing circuitry 110 may include one or more instances of a processor 112 and memory 114 that may be in communication with or otherwise control a user interface 130. As such, the processing circuitry 110 may be embodied as a circuit chip (e.g., an integrated circuit chip) configured (e.g., with hardware, software or a combination of hardware and software) to perform operations described herein.

The user interface 130 may include one or more interface mechanisms or devices for enabling communication with a user (e.g., a laptop computer). In some cases, the user interface 130 may be any means such as a device or circuitry embodied in either hardware, or a combination of hardware and software that is configured to receive and/or transmit data from/to devices or components in communication with the processing circuitry 110 via internal and/or external communication mechanisms. Accordingly, for example, the user interface 130 may further include wired and/or wireless communication equipment for at least communicating between a user, a downstream element 190, and the TEENI device 1, and/or other components or modules described herein.

The processor 112 may be embodied in a number of different ways. For example, the processor 112 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 112 may be configured to execute instructions stored in the memory 114 or otherwise accessible to the processor 112. As such, whether configured by hardware or by a combination of hardware and software, the processor 112 may represent an entity (e.g., physically embodied in circuitry—in the form of processing circuitry 110) capable of performing operations according to embodiments of the present invention while configured accordingly. Thus, for example, when the processor 112 is embodied as an ASIC, FPGA or the like, the processor 112 may be specifically configured hardware for conducting the operations described herein. Alternatively, as another example, when the processor 112 is embodied as an executor of software instructions, the instructions may specifically configure the processor 112 to perform the operations described herein in reference to execution of an example embodiment.

In some embodiments, the memory 114 may include one or more non-transitory memory devices such as, for example, volatile and/or non-volatile memory that may be either fixed or removable. The memory 114 may be configured to store information, data, applications, instructions or the like for enabling the processing circuitry 110 to carry out various functions in accordance with exemplary embodiments of the present invention. For example, the memory 114 may be configured to buffer input data for processing by the processor 112. Additionally or alternatively, the memory 114 may be configured to store instructions for execution by the processor 112. As yet another alternative or additional capability, the memory 114 may include one or more databases that may store or buffer a variety of data sets or tables useful for operation of the modules described below and/or the processing circuitry 110. Among the contents of the memory 114, applications or instruction sets may be stored for execution by the processor 112 in order to carry out the functionality associated with each respective application or instruction set. In particular, the memory 114 may store executable instructions that enable the computational power of the processing circuitry 110 to be employed to improve the functioning of the TEENI device 1 as described herein. In this regard, the TEEN device may be configured to regenerate the transected nerve to form a regenerated nerve. In some embodiments, for example, processing circuitry of the control element described above may be configured to detect neural activity as a signal in the regenerated nerve, amplify the signal, and record the neural activity in the regenerated nerve. In further embodiments, for instance, the processing circuitry may be configured to stimulate the regenerated nerve. As such, the improved operation of the computational components of the TEENI device 1 transforms the TEENI device 1 into a more capable tool for supporting a transected nerve as described herein.

In addition, in accordance with certain embodiments, the system may include certain packaging to protect the elements of the TEENI device from the conditions in the body once implanted. In some embodiments, for example, the packaging may comprise any dielectric adhesive and/or encapsulant that provides electrical insulation and moisture barrier properties (e.g., silicones, polyurethanes, epoxies, and/or the like), as understood by one of ordinary skill in the art. FIGS. 26A-B, for example, illustrate packaging for the system in accordance with certain embodiments of the invention. As shown in FIG. 26A, anisotropic conductive adhesive (ACA) may be used to electrically connect the TEENI device to PCBs, and a flip-chip bonder may be used to align, press, and cure the packaged system at, by way of example only, 150° C. FIG. 26B illustrates certain exemplary steps in packaging the system. For example, image B1 of FIG. 26B shows an ACA-bonded TEENI-PCB, image B2 shows 40 AWG wires soldered to PCB vias, and image B3 shows encapsulation of the system in a bilayered package including a medical grade epoxy (e.g., LOCTITE® M-31CL Hysol Medical Device Adhesive from Henkel Adhesives) and a silicone elastomer (e.g., BLUESIL™ RTV 3040 from Elkem Silicones).

III. Method of Supporting a Transected Nerve

Figure 15:
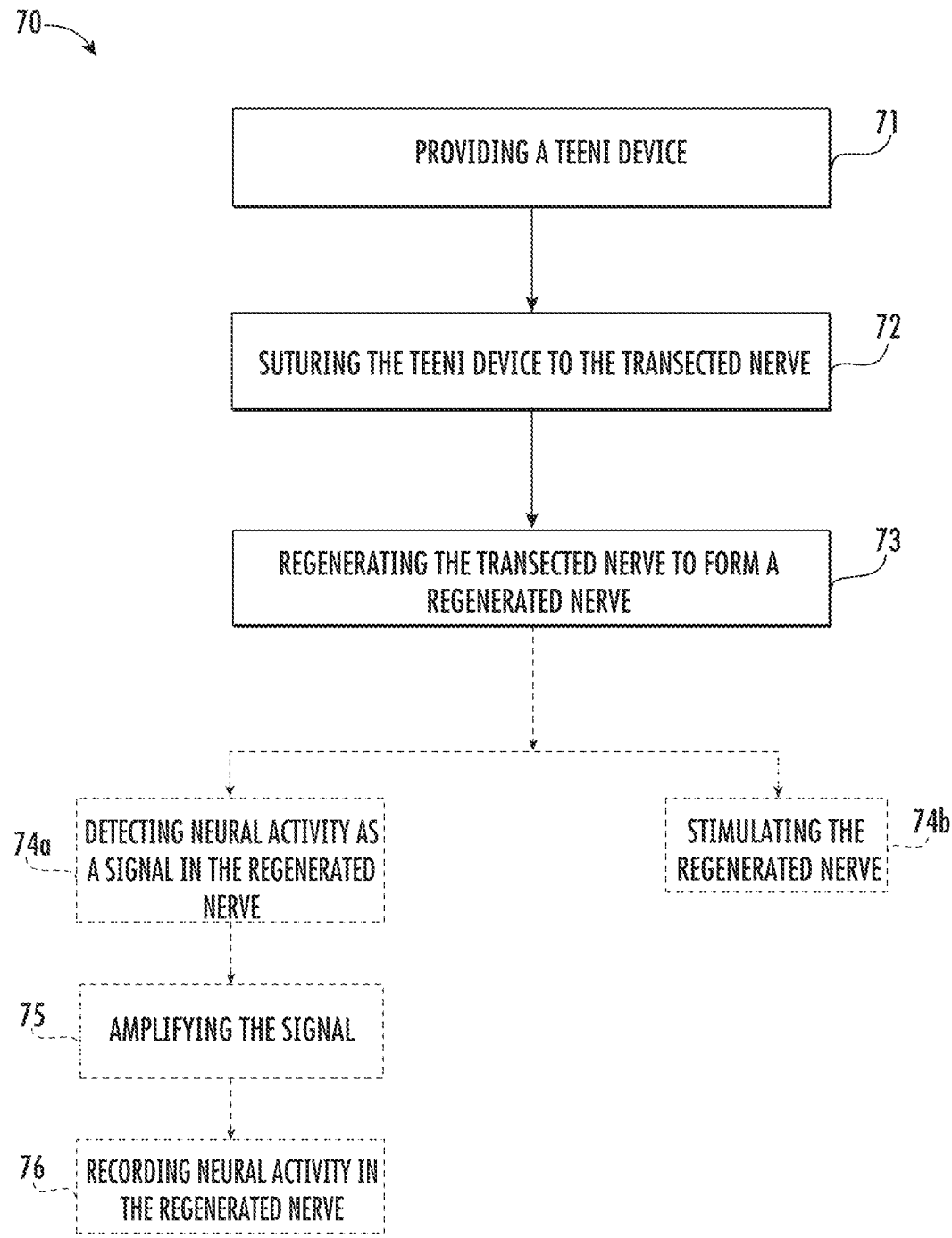
FIG. 15 is a block diagram of a method of supporting a transected nerve in accordance with certain embodiments of the invention.

In yet another aspect, certain embodiments according to the invention provide methods for supporting a transected nerve. FIG. 15 is a block diagram of a method of supporting a transected nerve in accordance with certain embodiments of the invention. As shown in FIG. 15, the method 70 may include providing a TEENI device at operation 71, suturing the TEENI device to the transected nerve at operation 72, and regenerating the transected nerve to form a regenerated nerve at operation 73. The method may further include the optional steps of detecting neural activity as a signal in the regenerated nerve at operation 74a, amplifying the signal at operation 75, and recording neural activity in the regenerated nerve at operation 76. Moreover, the method may include the optional step of stimulating the regenerated nerve at operation 74b. FIG. 18, for example, shows a system including a TEENI device implanted in a rat sciatic nerve transection in accordance with certain embodiments of the invention.

EXAMPLES

The following examples are provided for illustrating one or more embodiments of the present invention and should not be construed as limiting the invention.

Example 1

The TEENI thread sets were microfabricated using photolithography and thin-film metal-deposition processes adapted from. Briefly, a 5-μm-thick layer of polyimide (PI) (UVarnish-S, UBE Inc., Japan) was spin-coated on a silicon wafer and cured at 450° C. in nitrogen environment using a vendor-provided temperature-ramp profile spanning ~5 hours. Electrode sites, interconnect traces, test structures, and connector pads were patterned using 2.5-μm-thick layer of image-reversal resist AZ 1512 (Integrated Micromaterials, Texas, USA). A 50-nm-thick layer of Ti was sputter-deposited to facilitate adhesion between the first PI layer and platinum of the 300-nm-thick stack of Pt/Au/Pt (100 nm each) metal layer. Following metal deposition, the photoresist was lifted off by submerging the wafer in acetone for a few hours with gentle sonication. Subsequently, a second 5-μm-thick layer of PI was spin-coated and cured using the same temperature ramp-profile. A 26-μm-thick layer of positive photoresist (AZ 9260) was used as a mask to expose the electrode sites and connector contact-pads from the overlying PI layer using oxygen-plasma (Unaxis Shuttlelock Reactive Ion Etcher). The same process was used in the final step to etch the physical outline of the thread sets and the individual thread sets released from the silicon wafer with sharp tweezers.

EIS measurements were conducted using Autolab PGSTAT128N (Metrohm, USA) in potentiostatic mode over the frequency range of 10 to 30,000 Hz (5 points per decade, 10 mV sinusoidal perturbation voltage) to characterize the microfabricated electrode sites and overall electrical integrity of the fully assembled TEENI device. Measurements were carried out in room-temperature phosphate buffered saline (pH of 7.4), with an Ag—AgCl reference electrode and a large platinum counter electrode.

Example 2

A combination of collagen I, laminin, and MAHA was used to yield a photocrosslinkable hydrogel composite. In order to determine the optimal composite, a combination of selected components in varying concentrations were evaluated as provided in the table below.

| Group Name | Composition (mg/mL) | | | |
| --- | --- | --- | --- | --- |
| | Collagen I | Laminin | MAHA | GMHA |
| Low MAHA | 3 | 1.5 | 3 | — |
| High MAHA | 3 | 1.5 | 6 | — |
| GMHA | 3 | 1.5 | — | 5 |

Briefly, a solution of Dulbecco's modified eagle medium and HEPES was mixed with collagen I solution. Then, Cultrex 3D Culture Matrix Mouse Laminin I (Trevigen, Gaithersburg, Md.) and the HA-components were mixed with the collagen I solution. This pre-hydrogel solution was incubated at 37° C. for 30 minutes and crosslinked by 5 minutes of UV exposure. To synthesize HA components, 500 mg hyaluronic acid (HA) was dissolved overnight in a mixture of deionized water (25 mL) and acetone (25 mL) (GMHA) or in only deionized water (50 mL) (MAHA). GMHA was made by mixing trimethylamine (3.6 mL) and glycidyl methacrylate (3.6 mL) overnight and adding methacrylic anhydride (1.896 mL) dropwise to the HA solution on ice to yield MAHA. The reaction pH was maintained between 8 and 11 and continued overnight at 4° C. The GMHA and MAHA products were precipitated twice in acetone and ethanol, respectively and then lyophilized for 7 days to make them lyophilized and photocrosslinkable.

For mechanical testing, hydrogels were fabricated by pipetting 150 μL of pre-hydrogel solution into an 8-mm-diameter round mold and crosslinked as described above. Viscoelastic properties of the hydrogels were tested using a rheometer (Anton Paar, GmbH, MCR, Graz, Austria). Briefly, the sample was loaded onto the bottom plate of the device and water added to the humidity chamber at a temperature of 37° C. The top plate was then lowered until contact with the hydrogel was made. Shear storage and loss moduli were determined at an amplitude of 0.5% strain and over an angular frequency range of 0.1 to 100 rad/s. Storage moduli reported at an angular frequency of 1 rad/s. Young's modulus was determined using a materials testing machine (Instron Model 5942 Universal Test System, Norwood, Mass.) with uniaxial unconfined compression at a rate of 10 mm/min.

Figure 10:
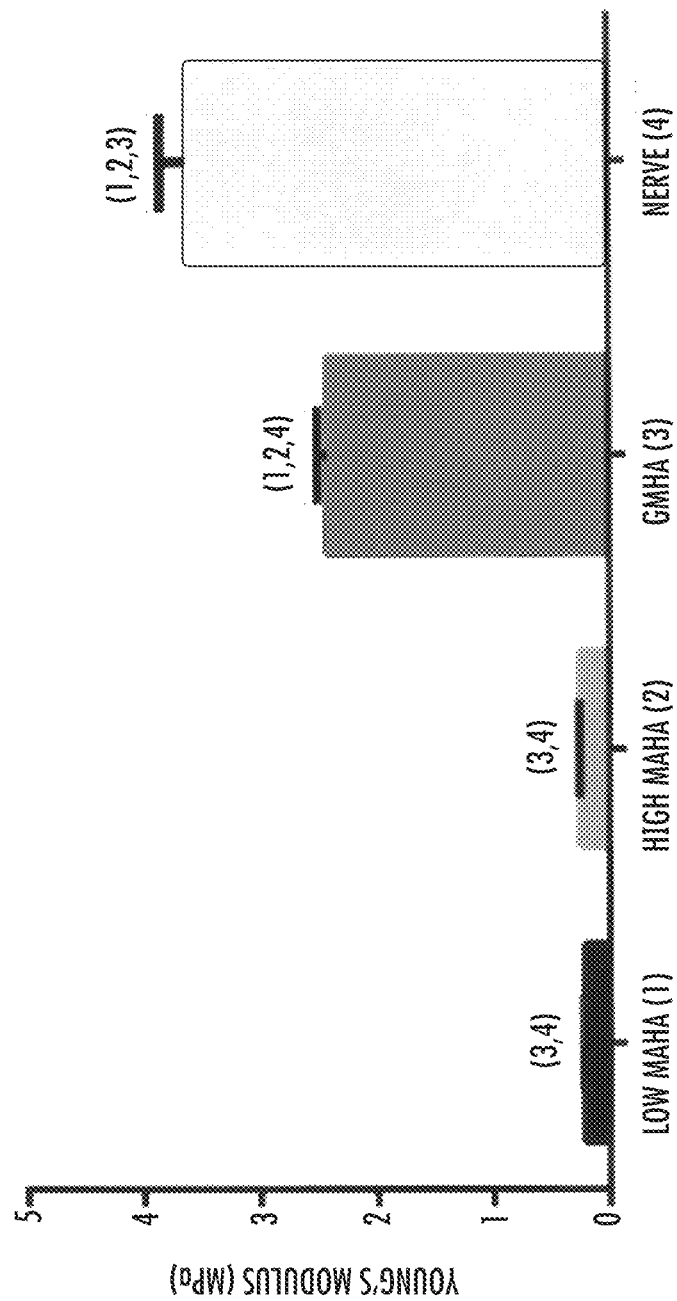
FIG. 10 illustrates Young's moduli from uniaxial unconfined compression on 3-component hydrogels and nerve in accordance with certain embodiments of the invention.
Figure 11B:
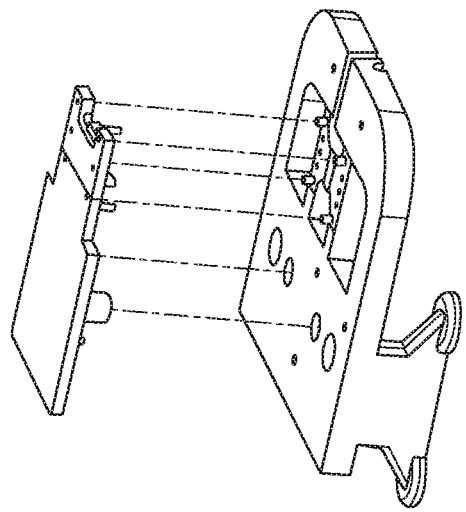
FIGS. 11A-11D show various components of a TEENI interface assembly in accordance with certain embodiments of the invention.
Figure 11D:
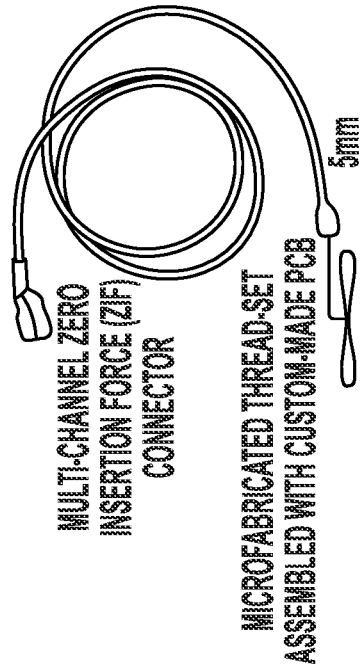
Figure 11A:
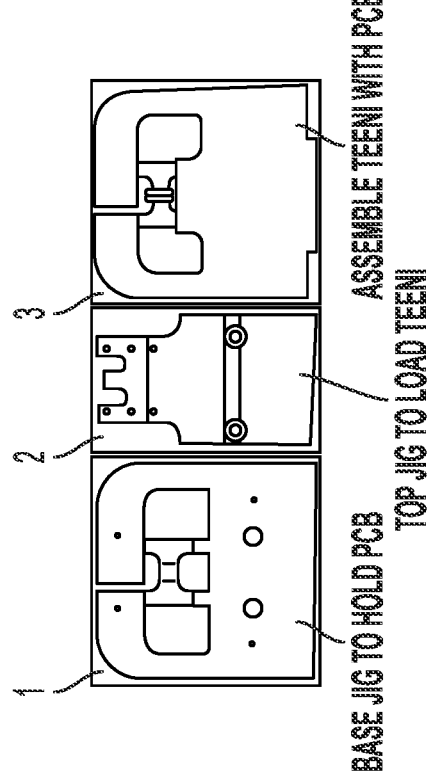
Figure 11C:
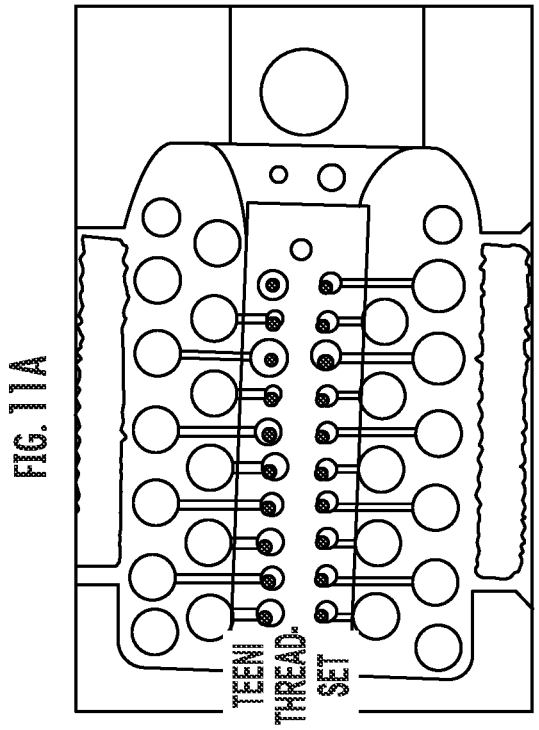

In addition to being mechanically compliant, hydrogels used in the TEENI devices must be robust enough to physically support the threads during assembly, implantation and after nerve regeneration. For example, FIGS. 30A-E show neurofilament growth using hydrogels in accordance with certain embodiments of the invention. All three hydrogel groups studied here were determined to be able to provide structural support for the integrated polyimide thread sets during device assembly and implantation. Results from rheology indicate that 3-component GMHA hydrogels had the highest storage modulus at 440±134 Pa and were significantly higher than that of a rat sciatic nerve at 20.3±7.7 Pa. The MAHA-based hydrogels had lower storage moduli than GMHA-based hydrogels with 66.4±22.8 Pa for 3-component Low MAHA and 176±49 Pa for 3-component High MAHA. Interestingly, the results from rheology indicated that the nerve trended toward having a lower storage modulus than that of the hydrogels. The Young's moduli from uniaxial unconfined compression are shown in FIG. 10. Three-component MAHA hydrogels were the least stiff with Young's moduli of 0.201±0.016 MPa and 0.258±0.007 MPa for Low and High, respectively. 3-component GMHA had a significantly higher Young's modulus of 2.43±0.08 MPa while rat sciatic nerve had a Young's modulus of 3.64±0.21 MPa. The results from uniaxial compression show that the hydrogels are less stiff than that of fresh rat sciatic nerve.

Example 3

Figure 12:
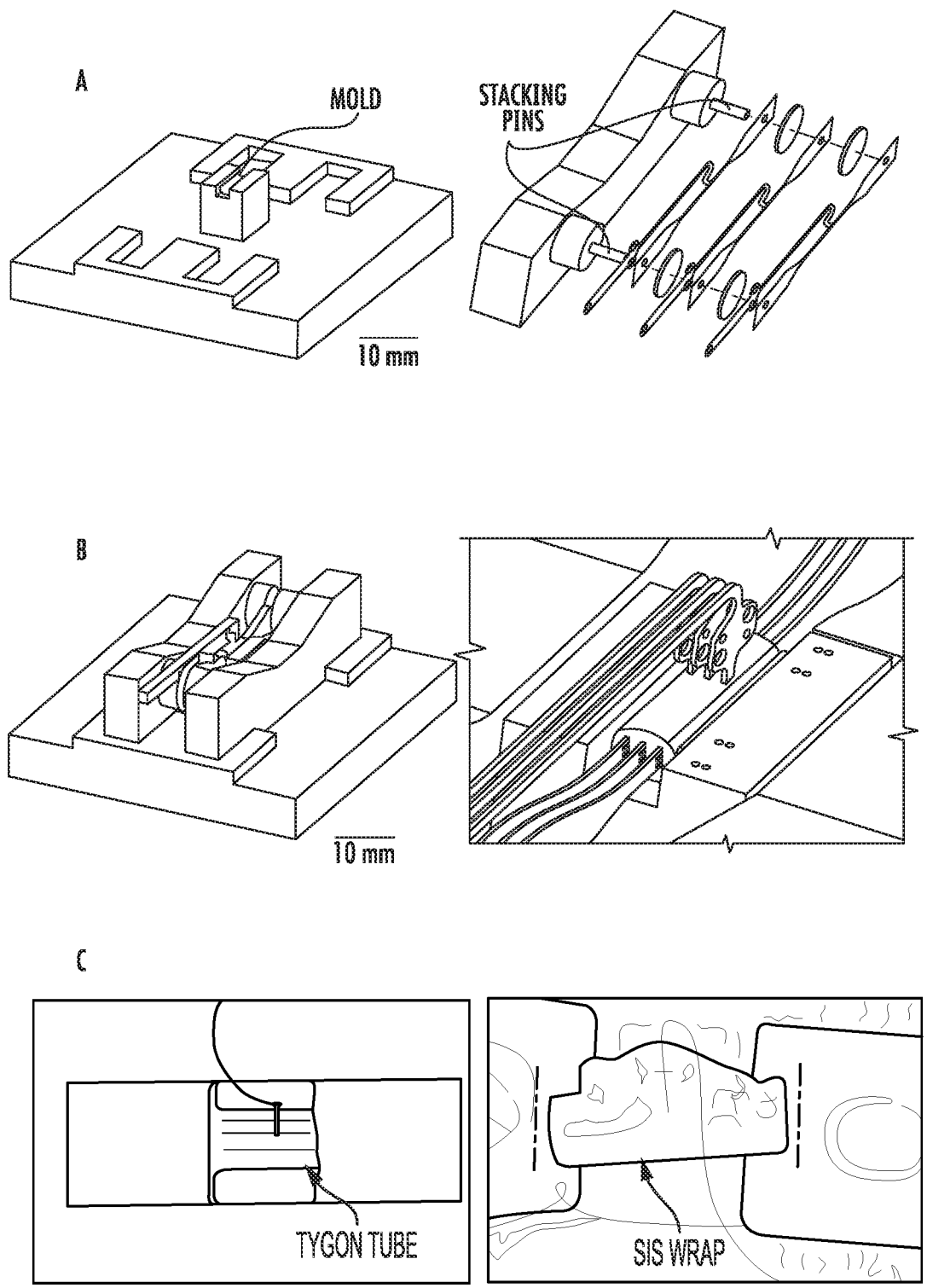
FIG. 12 illustrates an assembly process of a TEENI device in accordance with certain embodiments of the invention.

Microfabricated 3-thread and 4-thread sets were integrated within the hydrogel scaffold using custom-designed (SolidWorks) and 3D printed 2-part-assembly jigs as shown in FIG. 12. The thread sets were stacked together on the jig-fixture using 1-mm-diameter metal pins with 290-μm-thick spacers alternating between them to spatially distribute the threads throughout the volume of the rat sciatic nerve which has ~1 mm diameter (FIG. 12A). The thread-set-loaded fixture was then positioned on the jig-base such that the nerve-implant region was secured within a 5-mm-long and 1.5-mm-diameter tubular recess that held a Tygon tube serving as a mold for the hydrogel-thread-set integration. Pre-hydrogel solution was pipetted into the tube and cross-linked, as described earlier (FIG. 12B). The Tygon tube was then removed and the hydrogel-thread-set device assembly wrapped in decellularized resorbable small intestinal submucosa (SIS, Cook Biotech, USA). The thread sets were also sutured to the SIS via the suture holes in the polyimide interconnect structure for additional positional stability during surgical handling and to sustain flexural stresses post-implantation (FIG. 12C).

For example, FIGS. 8A-8E illustrate an assembly process of a TEENI device in accordance with certain embodiments of the invention. As shown in FIGS. 8A-8E, multiple thread-sets were stacked on side molds, side molds were assembled and placed in a base, decellularized small intestinal submucosa (SIS) and side molds were placed in the tubular mold portion of the base, hydrogel was injected on the SIS and around the threads, the hydrogel was crosslinked, and the ends of the threads were cut and the SIS sutured closed before implantation.

Impedance measurements were used to characterize the electrical properties of the newly microfabricated TEENI thread sets. Preliminary results from three fully assembled Gen1 TEENI devices confirmed the expected trend of inverse relationship between surface area of exposed platinum electrodes and their impedances across the entire measured frequency range. Specifically, impedances (mean±SD) at 1 kHz for electrodes with 200, 400, 800, 1600 $\mu m^2$ areas were 1442±171 k$\Omega$ (n=7), 893±354 k$\Omega$ (n=7), 485±151 k$\Omega$ (n=7), and 284±41 k$\Omega$ (n=8), respectively. These values are also consistent with those reported for thin-film platinum-based microelectrodes. EIS measurements are also useful to confirm electrical continuity throughout a multichannel zero insertion force (ZIF)-connector/PCB/thread-set entity and troubleshoot the assembly processes.

Example 4

A TEENI device was manufactured to have individual threads with functional electrodes implanted between the two nerve ends, four suture holes (200 $\mu m$ diameter) along the lead-body to secure thread sets in the implanted position, and large polyimide wings positioned at each end that have 1-mm-diameter holes to facilitate loading of the thread sets into custom-made jigs for assembly with the hydrogel-SIS scaffold. It also has connector pads to bond to a printed-circuit board (PCB) for data acquisition from the fully assembled TEENI device. The polyimide wings are cut off after assembly and prior to surgical implantation. Their purpose is to ensure precision assembly and to avoid damage during manual manipulation of thread sets (e.g., using sharp tweezers). It is important to avoid crack propagation in the dielectric, moisture ingress, or loss of electrical continuity. Each thread set was designed to have 3 or 4 threads and each thread was 10 $\mu m$ thick, 86 $\mu m$ wide, and 5-mm-long with a 170-$\mu m$-wide edge-to-edge gap between threads in a thread set. Each thread had 4 different recording electrodes with surface area of 200, 400, 800, and 1600 $\mu m^2$. These sizes were chosen to obtain an impedance range of 100 to 1,000 k$\Omega$, which is favorable for single-unit neural recording based on empirical evidences.

Also, a reference electrode, a stimulation electrode, and integrated test structures for assessment of dielectric integrity and electrical continuity of connecting leads were incorporated in the thread set. These "house-keeping" test-structures are a unique feature of the design, which enable evaluation of the reliability of the TEENI device in vivo and separate identification of abiotic and biotic causes of electrode-failures in longitudinal studies. All electrically functional components were designed to be 1 mm away from either end of the threads in order to avoid potential damage when the auxiliary wings are cut after device assembly. An additional large reference electrode was included in the leads outside of the nerve-implant region so that signals from muscles surrounding the nerve can be captured and used to attenuate unwanted EMG contamination.

FIGS. 11A-11D show various components of a TEENI interface assembly in accordance with certain embodiments of the invention. For example, FIGS. 11A-11D show the multichannel ZIF connector (Tucker Davis Technologies, Alachua, Fla., USA) for assembling individual thread sets to enable long-term in vivo acquisition of electrochemical and electrophysiological data. The micro-fabricated TEENI was designed to have 20-contact pads to bond via conductive silver epoxy to pads on a custom-designed printed-circuit board (PCB), which is further soldered to a percutaneous fine wire bundle that connects to an external ZIF connector.

Example 5

Figure 13:
FIG. 13 shows myelin profiles from immunolabeling with various antibodies on the TEENI device in accordance with certain embodiments of the invention.

The TEENI device and system were also tested for myelination. For example, FIG. 13 shows myelin profiles from immunolabeling with various antibodies on the TEENI device in accordance with certain embodiments of the invention. Twenty-micron-thick tissue sections sampled from mid-graft were double immunolabeled with various antibodies. The first image on the left of FIG. 13 shows results for antibodies against axons and laminin, the middle image of FIG. 13 shows results for antibodies against Schwann cells and nuclei, and the image on the right of FIG. 13 shows histological staining with Sudan Black to identify myelin profiles.

Example 6

The microfabrication process used to produce the TEENI polymer-metal electrode arrays shown in FIG. 7 began with blank 100-mm diameter silicon wafer. After cleaning in piranha, which forms a thin native oxide layer, the wafers were treated with HMDS and a 5 $\mu m$-thick layer of BPDA-PDA polyimide (PI) precursor (U-Varnish S, UBE Ind.) was formed by spin coating. After the PI was cured (max temp=350° C.) in a N2 atmosphere, its surface was activated in a reactive-ion-etching (RIE) $O_2$ plasma immediately before a 250-nm-thick layer of stoichiometric (1:1 Si:C) a-SiC:H was deposited via PECVD (Unaxis 790, Plasma-Therm, LLC) at 300° C. and 200 W with 5% $SiH_4$/He, $CH_4$, and He gasses (FIG. 7a). Using a 3-$\mu m$-thick layer of negative photoresist (nLOF 2035, MicroChemicals GmbH) as a lift-off mask, a stack of thin metal layers (Ti: 50 nm, Pt: 100 nm, Au: 100 nm, Pt: 100 nm, Ti: 50 nm) were deposited by sputtering (CMS-18 multi-source, Kurt K. Lesker Company) (FIG. 7b). After soaking in NMP at 70° C. and some sonication, the excess metal was lifted off. A second 250-nm-thick layer of a-SiC:H film was deposited as before (FIG. 7c). Both layers of a-SiC:H were patterned by an SF6 RIE/ICP dry etch (Unaxis SLR, Plasma-Therm, LLC.) with a thin positive photoresist (AZ1512, MicroChemicals GmbH) as the etch mask (FIG. 7d). After the residual surface organics were removed by an $O_2$ plasma etch and an aminopropyl triethoxysilane adhesion agent (VM-652, HD Microsystems) was applied, a second 5-μm-thick layer of polyimide precursor was formed by spin coating (FIG. 7e). The Pt electrode sites and connector pads were revealed by an RIE/ICP dry etch in $O_2$ and $SF_6$ plasmas using a 10-μm-thick layer of positive photoresist (AZ9260, MicroChemicals GmbH) as an etch mask (FIG. 7f). To form the shape of the TEENI device, both layers of PI were etched in a single $O_2$ plasma etch using a 25-μm-thick layer of positive photoresist (AZ9260, MicroChemicals GmbH) as an etch mask (FIG. 7g). Finally, the TEENI devices were carefully removed from the carrier wafer using tweezers (FIG. 7h).

After the TEENI devices were microfabricated, they were attached to a small circuit board that soldered to a long bundle of fine wires that are soldered on the other end to an external circuit board with a high-channel-count connector convenient for impedance assessment and electrophysiological measurements. Because the small circuit board attached to the TEENI was to be implanted, it was potted in silicone. The implant was then sterilized and the distal TEENI component was integrated into a biodegradable hydrogel composite scaffold that was wrapped in a bioresorbable small intestinal submucosa (SIS) and sutured to the ends of a transected nerve. 250 gm Lewis Rats (LEW/Crl) from Charles River Laboratories (Kingston, N.Y.) were used and 5-mm-long sciatic nerve gaps were formed in the rats that were filled by the TEENI device.

Surprisingly, as shown in FIG. 23, strong single-unit recordings were observed at the distal electrodes after only 4 days. As shown in FIG. 26, recordings with good signal-to-noise ratio (SNR) were observed for 6 weeks, at which point recording was no longer possible due to head-cap failure (i.e., the structure securing the external connector to the implanted TEENI to the skull). As shown in FIGS. 19-20, explantation of the TEENI devices revealed that they were well integrated into tissue, exhibited extensive vascularization associated with healthy tissue, and had a significant number and distribution of axons through the scaffold and near the TEENI devices.

However, histological sectioning of regenerated nerve/device interfaces revealed the consistent presence of encapsulating tissue primarily composed of fibroblasts and macrophages that surround each polyimide thread, as shown in FIGS. 21A-E. The presence of this foreign body response (FBR) around electrode sites can reduce the ability to record/stimulate adjacent neuronal cells and could lead to device rejection. Indeed, as shown in FIG. 22, impedance on channels was generally stable over 6 weeks, and the discovery of the FBR around the electrode sites explains the SNR reduction seen after three weeks.

Example 7

To rapidly assess the robustness of implanted electronic devices, it is common to perform soak tests at elevated temperatures. Given the exponential dependence of thermally driven processes on temperatures (i.e., the Arrhenius relationship), raising the temperature from ~37° C. (body temperature) to 87° C. results in an acceleration factor of ~32×. However, for soak tests to be predictive, the failure modes should be preserved at higher temperatures. For implanted devices, some failures are driven by the aggressive chemical environment (e.g., reactive oxygen species) generated by activated immune cells. However, because the oxygen concentration of saline drops significantly at higher temperatures, it is common for implants to do well with short hot saline-only soak tests and yet fail when implanted for an equivalent time period. A better method is to use a reactive-accelerated-aging (RAA) soak test that employs hydrogen peroxide as a source of reactive oxygen species to simulate the chemistry of the solution surrounding chronic implants.

Because delamination of insulating dielectric layers from the conductive metal layers within neural interfaces has been shown to be a significant failure mode, RAA soak tests were performed on TEENI electrodes prepared in accordance with Example 9 to rapidly assess different combinations of thin films to promote good adhesion between the polyimide and platinum layers in the TEENI. Specifically, 10 to 20 mM of $H_2O_2$ in phosphate buffered saline at 85-87° C. was used and tested for 3 days, which is equivalent to a 3.2-month implantation (ASTM F1980). The results shown in FIG. 27 illustrate the significant reduction in impedance (at 1 KHz) observed for different sized electrodes on TEENI made with different combinations of polyimide and various thin adhesion-promoting films. As expected, TEENI made without using an adhesion layer (i.e., for PI—Pt—PI, PI—Pt—Au—Pt—PI) did not maintain electronic integrity (i.e., impedance dropped by 50 to 95%). Although the addition of titanium as an adhesion layer sometimes resulted in improved outcomes (i.e., impedance dropped by 20 to 30%), the combination of silicon carbide and titanium yielded extremely robust results (i.e., impedance changed by <±5%). FIG. 28 shows that this robustness exists over the entire frequency band of interest for neural interfaces. Subsequent experiments performed for 7 days confirmed the excellent robustness of the PI—SiC—Ti—Pt—Au—Pt—Ti—SiC—PI material stack inside the TEENI devices. No other peripheral nerve interface has been soak tested as harshly and survived with excellent functionality.

Example 8

TEENI neural electrodes were microfabricated in a class 100/1000 cleanroom using photolithography, thin-film deposition, and dry etching processes. In particular, 5 μm of BPDA-PDA polyimide (U-Varnish S, UBE Ind.) was spin coated on a 100-mm-diameter Si wafer and cured at 350° C. under $N_2$. The PI surface was activated in a reactive-ion-etching (RIE) $O_2$ plasma and then coated by a 250-nm-thick film of stoichiometric a-SiC:H formed by plasma enhanced chemical vapor deposition (PECVD) at 300° C. Electrode sites, interconnect traces, test structures, and connector pads were formed by a 400-nm-thick Ti+Pt/Au/Pt+Ti metal stack that was patterned by a lift-off process using image-reversal photoresist (nLOF 2035, MicroChemicals GmbH). The metal patterns were sealed by a 2nd film of a-SiC:H that was then coated with an aminopropyl triethoxysilane silane (APTES) agent (VM-652, HD Microsystems) followed by 5 μm of polyimide, deposited and cured as previously discussed. Electrode sites, connector pads, and thread-set geometry were patterned by RIE dry etching using $O_2$ (to remove PI) and $SF_6$ (to remove Ti and a-SiC:H) plasmas.

The primary abiotic failure mechanisms that the device can suffer from include: (1) PI—PI delamination/degradation leading to shorting between adjacent metal structures, (2) PI-metal delamination resulting in changes to electrode area or failure, and (3) metallic fracture resulting in open circuits. The adhesive strength between polymers and metals are notoriously poor due to the lack of significant chemical bond formation. As shown in FIG. 24, three different TEENI device designs were fabricated to probe these failure mechanisms. Design A did not use a-SiC:H and resulted in only PI—PI or PI-metal interfaces. Design B used a conformal a-SiC:H adhesion layer producing both PI—SiC—PI and PI—SiC-metal interfaces. Design C used $SF_6$ patterned a-SiC:H that resulted in PI—PI, PI—SiC—PI, and PI—SiC-metal interfaces. All designs maintained a 4 µm overlap of PI around exposed metal sites, and Design C used a 6 µm overlap of a-SiC:H around all metal.

During fabrication, qualitative assessments were made about the differing adhesive strengths between material interfaces and fabrication methodologies. Metal traces on Design A would sporadically delaminate during lift-off due to residual film stress and poor interfacial adhesion between PI and Ti—Pt/Au/Pt—Ti. Delamination was also evidenced during initial testing for Designs B and C, when a-SiC:H was used with Pt/Au/Pt stacks without Ti. However, delamination during lift-off was completely eliminated with the addition of a Ti layer due to its strong adhesion to the native $SiO_2$ layer on SiC. Furthermore, PI—SiC delamination occurred at the top PI layer if the APTES agent was not used.

Devices were characterized by electrical impedance spectroscopy (EIS) using a PGSTAT302N (Metrohm Autolab) and a probe station. EIS spectra were obtained using a 3-electrode setup with a TEENI working electrode, Pt wire counter electrode, and a 3 M KCl Ag/AgCl reference electrode in a 10 mM PBS electrolyte from 100 kHz to 10 mHz. No DC offset with respect to the open circuit potential was applied. RAA soak tests were performed in 10 to 20 mM $H_2O_2$ PBS at 87° C. to assess in vitro electrode durability. $H_2O_2$ concentration ($[H_2O_2]$) was maintained by replenishing 8.75 mM of $H_2O_2$ per hour via a syringe pump. $[H_2O_2]$ was verified by measuring the absorbance at 407 nm using a titanium (IV) oxysulfate (Milipore Sigma) colorimetric assay with a dilution factor of 15 in conjunction with Beer's law. Three microelectrode arrays per device design were tested with a total of 44 electrodes that ranged in size from 200 to 16,000 $\mu m^2$.

EIS characterization of as-fabricated devices revealed expected dependencies between electrical impedance and exposed electrode area and typical phase-angle behavior, as shown in FIG. 30. Devices were subjected to 3-day and 7-day RAA experiments at 87° C., which corresponds to ~3 and ~7 months in vivo respectively. Observed changes to EIS behavior were correlated to abiotic failure mechanisms. After 3-day RAA, Design-A devices with no a-SiC:H showed widespread PBS penetration between the PI-metal-PI interface and partial delamination of the exposed electrode metal as evidenced by warping/bubbling of the metal layer, as shown in FIG. 25 A1. The EIS spectra for 44 electrodes decreased by −32±9% (arithmetic average±stdv) at 1 KHz confirming an increase in the active electrode area that could interface with the electrolyte resulting from partial delamination of the PI-metal interface, as shown in FIG. 29. Furthermore, 3 of 44 electrodes had significant cracks along the exposed metal that resulted in open circuits. After 7-day RAA, Design-A devices showed extensive delamination and/or loss of exposed metal from the underlying PI, as shown in FIG. 25 A2, rendering further EIS characterization using a probe station difficult. Ti—PI interfacial strength is primarily due to mechanical interlocking instead of strong chemical bonding, and RAA experimentation was effective at highlighting the weakness of titanium as an effective adhesion layer to PI for neural interfacial implants. No PI—PI delamination was observed at either 3-day or 7-day RAA.

Both Designs B and C that used a-SiC:H adhesion layers between PI and metal exhibited an increased ability to resist abiotic failure. After 3-day RAA, there was no optically detected damage to any electrode sites, metal traces, or material interfaces, as shown in FIGS. 25 B1 & C1, and EIS data showed minimal change after soaking with −0.9±1.9% and −7.6±9.5% average change at 1 KHz for Designs B and C, respectively, as shown in FIG. 29. After 7-day RAA, there was still no optically detected metal-SiC delamination confirming SiC's ability to effectively chemically bond with titanium through Ti—C and/or Ti—Si. However, the PECVD deposited a-SiC:H formed a highly compressive (~−350 MPa) film that led to sporadic residual stress induced fracturing of the a-SiC:H layer at high radius of curvature areas (e.g. around electrode sites and along curved metal traces) during RAA, as shown in FIGS. 25 B2 & C2. These cracks led to PBS penetration and partial delamination of the weaker SiC—PI interface.

EIS analysis of 7-day RAA soaked devices, as shown in FIG. 31, confirmed that a-SiC:H cracking led to breaks in some metal traces resulting in open-circuits on 5/44 and 4/44 electrodes for design B and C, respectively. Another 2/44 and 6/44 electrodes experienced a significant decrease in impedance with a corresponding bimodal-phase plot indicating capacitive behavior at high frequencies and resistive at low with a local maximum between 10-100 Hz. There was also sporadic optical evidence of PBS penetration at the PI—SiC interface around some electrode sites; however, this delamination was not completely correlatable with the previously mentioned impedance drops suggesting that the SiC-metal interface was not compromised. The EIS spectra of the majority remaining 37 and 34 "good" electrodes changed by only −7.2±7.4% and −11.7±6.8% at 1 KHz from the pre-soak values for Designs B and C, respectively.

Non-Limiting Exemplary Embodiments

Having described various aspects and embodiments of the invention herein, further specific embodiments of the invention include those set forth in the following paragraphs.

Certain embodiments provide devices, systems, and methods for regenerating a transected nerve to form a regenerated nerve, detecting and recording neural activity in the regenerated nerve, and stimulating the regenerated nerve. In one aspect, a tissue-engineered electronic peripheral nerve interface (TEENI) device is provided. The TEENI device may include a support member having a length, at least one thread set comprising a plurality of thread set arms having a plurality of electronic leads running through the thread set arms, the thread set arms being fully encapsulated within the support member, and a plurality of electrodes fixed to the thread set arms. According to certain embodiments, for example, the TEENI device may be configured to regenerate a transected nerve to form a regenerated nerve, detect and record neural activity in the regenerated nerve, and stimulate the regenerated nerve.

In accordance with certain embodiments, for instance, the support member may comprise a hydrogel-based scaffold. In some embodiments, for example, the support member may comprise a plurality of magnetically templated aligned microchannels such that a portion of the microchannels, a network of interconnected microchannels, or a combination thereof extend along the length of the support member. In certain embodiments, for instance, the TEENI device may further comprise a sheath enveloping the support member.

In accordance with certain embodiments, for example, the plurality of thread set arms may comprise a dielectric barrier material. In some embodiments, for instance, each of the plurality of thread set arms may comprise a width from about 1 µm to about 1000 µm and a thickness from about 1 µm to about 100 µm. In further embodiments, for example, when the TEENI device is sutured into a subject in need thereof, the plurality of thread set arms may be evenly distributed through a volume of the transected nerve equal to a transected nerve diameter multiplied by a distance between one or more nodes of Ranvier.

In another aspect, a system for supporting a transected nerve is provided. The system may include a TEENI device, a control element, a connecting element comprising a plurality of electronic leads connected to the TEENI device and extending to the control element, and a downstream element configured to communicate with the transected nerve via the control element. The TEENI device may include a support member, a thread set comprising a plurality of thread set arms having a plurality of electronic leads running through the thread set arms, the thread set arms being fully encapsulated within the support member, and a plurality of fixed electrodes to the plurality of thread set arms. In some embodiments, for example, the TEENI device may be configured to regenerate the transected nerve to form a regenerated nerve.

In accordance with certain embodiments, for instance, the control element may comprise processing circuitry configured to detect neural activity as a signal in the regenerated nerve, amplify the signal, and record the neural activity in the regenerated nerve. In some embodiments, for example, the processing circuitry may be configured to stimulate the regenerated nerve. In further embodiments, for instance, the control element may comprise a printed circuit board (PCB) or a flexible printed circuit (FPC).

According to certain embodiments, for example, the transected nerve may comprise a proximal nerve, and the downstream element may comprise a distal nerve. In such embodiments, for instance, the TEENI device may extend between the proximal nerve and the distal nerve. In other embodiments, for example, the transected nerve may comprise a proximal nerve, and the downstream element may comprise a prosthetic device. In such embodiments, for instance, the TEENI device extends from the proximal nerve to the connecting element.

In yet another aspect, a method for supporting a transected nerve is provided. The method may include providing a TEENI device, suturing the TEENI device to the transected nerve, and regenerating the transected nerve to form a regenerated nerve. The TEENI device may include a support member, a thread set comprising a plurality of thread set arms having a plurality of electronic leads running through the thread set arms, the thread set arms being fully encapsulated within the support member, and a plurality of electrodes fixed to the plurality of thread set arms.

In accordance with certain embodiments, for example, the method may further comprise detecting neural activity as a signal in the regenerated nerve, amplifying the signal, and recording neural activity in the regenerated nerve. In further embodiments, for instance, the method may further comprise stimulating the regenerated nerve.

Many modifications and other embodiments of the inventions set forth herein will come to mind to one skilled in the art to which the inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A tissue-engineered electronic peripheral nerve interface (TEENI) device comprising:
   a biomaterial support member having a length;
   at least one thread set comprising a plurality of thread set arms having a plurality of electronic leads running through the thread set arms, the thread set arms being fully encapsulated within the biomaterial support member; and
   a plurality of electrodes fixed to the thread set arms,
   wherein when the TEENI device is sutured into a subject in need thereof, the plurality of thread set arms are configured to be positioned at least partially within a transected nerve.

2. The device of claim 1, wherein the TEENI device is configured to:
   regenerate the transected nerve to form a regenerated nerve,
   detect and record neural activity in the regenerated nerve, and
   stimulate the regenerated nerve.

3. The device of claim 1, wherein the biomaterial support member comprises a hydrogel-based scaffold.

4. The device of claim 1, wherein the biomaterial support member comprises a plurality of magnetically templated aligned microchannels such that a portion of the microchannels, a network of interconnected microchannels, or a combination thereof extend along the length of the biomaterial support member.

5. The device of claim 1, wherein the plurality of thread set arms comprises a dielectric barrier material.

6. The device of claim 1, wherein each of the plurality of thread set arms comprises a width from about 1 μm to about 1000 μm and a thickness from about 1 μm to about 100 μm.

7. The device of claim 1, wherein when the TEENI device is sutured into a subject in need thereof, the plurality of thread set arms are evenly distributed through a volume of the transected nerve equal to a transected nerve diameter multiplied by a distance between one or more nodes of Ranvier.

8. The device of claim 1, further comprising a sheath enveloping the biomaterial support member.

9. A system for supporting a transected nerve, the system comprising:
   a tissue-engineered electronic peripheral nerve interface (TEENI) device, the TEENI device comprising:
      a biomaterial support member;
      a thread set comprising a plurality of thread set arms having a plurality of electronic leads running through the thread set arms, the thread set arms being fully encapsulated within the biomaterial support member; and
      a plurality of electrodes fixed to the plurality of thread set arms,
      wherein when the TEENI device is sutured into a subject in need thereof, the plurality of thread set arms are configured to be positioned at least partially within the transected nerve;
   a control element comprising processing circuitry configured to:
      detect neural activity as a signal in a regenerated nerve,
      amplify the signal,
      record the neural activity in the regenerated nerve, and
      stimulate the regenerated nerve;

a connecting element comprising a plurality of suture holes and a plurality of connecting element electronic leads connected to the TEENI device and extending to the control element; and a downstream element configured to communicate with the transected nerve via the control element.

10. The system of claim 9, wherein the TEENI device is configured to regenerate the transected nerve to form the regenerated nerve.

11. The system of claim 9, wherein the control element comprises a printed circuit board (PCB) or a flexible printed circuit (FPC).

12. The system of claim 9, wherein the transected nerve comprises a proximal nerve, and the downstream element comprises a distal nerve.

13. The system of claim 12, wherein the TEENI device is configured to be inserted between the proximal nerve and the distal nerve.

14. The system of claim 9, wherein the transected nerve comprises a proximal nerve, and the downstream element comprises a prosthetic device.

15. The system of claim 14, wherein the TEENI device is configured to be sutured to the proximal nerve and extend to the connecting element.

* * * * *

UNITED STATES PATENT AND TRADEMARK OFFICE
CERTIFICATE OF CORRECTION

PATENT NO. : 11,376,005 B2
APPLICATION NO. : 15/987388
DATED : July 5, 2022
INVENTOR(S) : Judy et al.

Page 1 of 1

It is certified that error appears in the above-identified patent and that said Letters Patent is hereby corrected as shown below:

In the Claims

<u>Column 22</u>
Line 46, "(TEENT)" should read --(TEENI)--

Signed and Sealed this
Thirtieth Day of August, 2022

Katherine Kelly Vidal
*Director of the United States Patent and Trademark Office*